United States Patent
Taylor

(10) Patent No.: US 11,070,895 B2
(45) Date of Patent: *Jul. 20, 2021

(54) SYSTEM AND METHOD FOR MONITORING GAS EMISSION OF PERISHABLE PRODUCTS

(71) Applicant: Walmart Apollo, LLC, Bentonville, AR (US)

(72) Inventor: Joseph D. Taylor, Pullman, WA (US)

(73) Assignee: Walmart Apollo, LLC, Bentonville, AR (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/990,397

(22) Filed: May 25, 2018

(65) Prior Publication Data
US 2018/0279023 A1   Sep. 27, 2018

Related U.S. Application Data

(63) Continuation of application No. 15/541,160, filed as application No. PCT/US2015/067902 on Dec. 29, 2015, now Pat. No. 10,009,667.
(Continued)

(51) Int. Cl.
*H04Q 9/00* (2006.01)
*G01N 33/02* (2006.01)

(52) U.S. Cl.
CPC ............. *H04Q 9/00* (2013.01); *G01N 33/02* (2013.01); *H04Q 2209/30* (2013.01); *H04Q 2209/40* (2013.01); *H04Q 2209/823* (2013.01)

(58) Field of Classification Search
CPC ....................................................... H04Q 9/00
See application file for complete search history.

(56) References Cited

U.S. PATENT DOCUMENTS

| 5,369,995 A | 12/1994 | Scheinbeim |
| 5,621,162 A | 4/1997 | Yun |

(Continued)

FOREIGN PATENT DOCUMENTS

| CA | 2469699 | 1/2016 |
| CN | 1789992 | 6/2006 |

(Continued)

OTHER PUBLICATIONS

U.S. Appl. No. 16/036,456, filed Jul. 16, 2018, Ckristian Velez.
(Continued)

*Primary Examiner* — Santiago Garcia
(74) *Attorney, Agent, or Firm* — Fitch, Even, Tabin & Flannery LLP

(57) ABSTRACT

A system for automatically monitoring merchandise in a retail sales environment is provided. The system includes a display fixture configured to store and display for sale a group of perishable items and one or more gas emission sensors associated with the display fixture and configured to measure gas emissions from the group of perishable items. The system further includes a control circuit coupled to the one or more gas emission sensors and configured to receive a gas emission measurement taken at the display fixture, compare the gas emission measurement with stored gas emission data associated with a category of the group of perishable items; and make a determination corresponding to the group of perishable items based on the comparison.

22 Claims, 4 Drawing Sheets

Related U.S. Application Data

(60) Provisional application No. 62/098,948, filed on Dec. 31, 2014.

(56) References Cited

U.S. PATENT DOCUMENTS

| | | | |
|---|---|---|---|
| 5,671,362 | A | 9/1997 | Cowe |
| 5,774,053 | A | 6/1998 | Porter |
| 5,791,497 | A | 8/1998 | Campbell |
| 5,835,012 | A | 11/1998 | Wilk |
| 6,012,834 | A * | 1/2000 | Dueck ................ G06Q 20/201 700/231 |
| 6,204,763 | B1 | 3/2001 | Sone |
| 6,285,282 | B1 | 9/2001 | Dorenbosch et al. |
| 6,294,997 | B1 | 9/2001 | Paratore et al. |
| 6,296,187 | B1 | 10/2001 | Shearer |
| 6,386,454 | B2 | 5/2002 | Hecht |
| 6,435,002 | B1 | 8/2002 | Briggs |
| 6,497,367 | B2 | 12/2002 | Conzola |
| 6,549,135 | B2 | 4/2003 | Singh |
| 6,600,418 | B2 | 7/2003 | Francis |
| 6,624,752 | B2 | 9/2003 | Klitsgaard |
| 6,779,722 | B1 | 8/2004 | Mason |
| 6,847,447 | B2 | 1/2005 | Ozanich |
| 6,865,516 | B1 | 3/2005 | Richardson |
| 6,876,990 | B2 | 4/2005 | Yamanishi |
| 6,965,871 | B1 | 11/2005 | Szabo |
| 6,970,100 | B2 | 11/2005 | Lovegreen |
| 6,982,640 | B2 | 1/2006 | Lindsay |
| 7,004,621 | B2 | 2/2006 | Roberts |
| 7,027,958 | B2 | 4/2006 | Singh |
| 7,057,495 | B2 | 6/2006 | Debord |
| 7,065,501 | B1 | 6/2006 | Brown |
| 7,148,803 | B2 | 12/2006 | Bandy |
| 7,185,810 | B2 | 3/2007 | White |
| 7,245,386 | B2 | 7/2007 | Philipps |
| 7,248,147 | B2 | 7/2007 | Debord |
| 7,271,720 | B2 | 9/2007 | Tabe |
| 7,271,724 | B2 | 9/2007 | Goyal |
| 7,298,257 | B2 | 11/2007 | Suzuki |
| 7,347,361 | B2 | 3/2008 | Lovett |
| 7,372,003 | B2 | 5/2008 | Kates |
| 7,434,724 | B2 | 10/2008 | Lane |
| 7,455,225 | B1 | 11/2008 | Hadfield |
| 7,487,913 | B2 | 2/2009 | Adema |
| 7,495,558 | B2 | 2/2009 | Pope |
| 7,543,741 | B2 | 6/2009 | Lovett |
| 7,560,013 | B2 | 7/2009 | Shekarriz |
| 7,673,464 | B2 | 3/2010 | Bodin |
| 7,675,424 | B2 | 3/2010 | Debord |
| 7,693,739 | B2 | 4/2010 | Schmidtberg |
| 7,757,947 | B2 | 7/2010 | Reznik |
| 7,775,130 | B2 | 8/2010 | Harish |
| 7,792,711 | B2 | 9/2010 | Swafford, Jr. |
| 7,796,038 | B2 | 9/2010 | Batra |
| 7,810,720 | B2 | 10/2010 | Lovett |
| 7,835,885 | B2 | 11/2010 | Ben-Tzur |
| 7,937,244 | B2 | 5/2011 | Kadaba |
| 7,954,712 | B2 | 6/2011 | Babcock |
| 7,960,176 | B2 | 6/2011 | Louvet |
| 7,978,060 | B2 | 7/2011 | Mandava |
| 8,072,605 | B2 | 12/2011 | Costa |
| 8,102,101 | B2 | 1/2012 | Giurgiutiu |
| 8,112,303 | B2 | 2/2012 | Eglen |
| 8,203,603 | B2 | 6/2012 | Harbert |
| 8,279,065 | B2 | 10/2012 | Butler |
| 8,306,871 | B2 | 11/2012 | Farmer |
| 8,334,970 | B2 | 12/2012 | Wildenbeest |
| 8,354,927 | B2 | 1/2013 | Breed |
| 8,412,590 | B2 | 4/2013 | Elliott |
| 8,447,665 | B1 | 5/2013 | Schoenharl |
| 8,682,760 | B2 | 3/2014 | Cameo |
| 8,786,407 | B2 | 7/2014 | Liu |
| 8,803,970 | B2 | 8/2014 | Weisensale |
| 8,870,453 | B2 | 10/2014 | Branch |
| 8,947,234 | B2 | 2/2015 | Doan |
| 8,994,508 | B2 | 3/2015 | Dacus |
| 9,024,755 | B2 | 5/2015 | Fuhr |
| 9,030,295 | B2 | 5/2015 | Allen |
| 9,031,990 | B2 | 5/2015 | Scott |
| 9,218,585 | B2 | 12/2015 | Gupta |
| 9,244,147 | B1 | 1/2016 | Soundararajan |
| 9,275,361 | B2 | 3/2016 | Meyer |
| 9,316,595 | B2 | 4/2016 | Wakita |
| 9,366,483 | B2 | 6/2016 | Eckhoff |
| 9,443,217 | B2 | 9/2016 | Iyer |
| 9,449,208 | B2 | 9/2016 | Luk |
| 9,514,323 | B2 | 12/2016 | Mehring |
| 9,557,224 | B2 | 1/2017 | Eisenstadt |
| 9,710,754 | B2 | 7/2017 | Kaye |
| 9,766,114 | B2 | 9/2017 | Ademe |
| 9,789,518 | B2 | 10/2017 | Iino |
| 9,811,632 | B2 | 11/2017 | Grabiner |
| 9,824,298 | B1 | 11/2017 | Krishnan |
| 9,835,498 | B2 | 12/2017 | Haarer |
| 9,888,214 | B2 | 2/2018 | Bateman |
| 9,915,638 | B2 | 3/2018 | Pakstaite |
| 10,009,667 | B2 | 6/2018 | Taylor |
| 10,049,397 | B1 * | 8/2018 | Patankar ............ G06Q 30/0631 |
| 10,060,798 | B1 | 8/2018 | Riscalla |
| 10,176,451 | B2 | 1/2019 | Nemet |
| 10,187,593 | B2 | 1/2019 | Holmes |
| 10,281,200 | B2 | 5/2019 | Johnston |
| 10,285,433 | B2 | 5/2019 | Ademe |
| 10,324,439 | B2 | 6/2019 | Lagares-Greenblatt |
| 10,373,472 | B2 | 8/2019 | Johnston |
| 10,386,827 | B2 | 8/2019 | Enver |
| 10,423,918 | B2 | 9/2019 | Mehring |
| 10,445,684 | B2 | 10/2019 | Mehring |
| 10,466,111 | B2 | 11/2019 | Jones |
| 10,546,162 | B1 | 1/2020 | Diorio |
| 10,552,654 | B2 | 2/2020 | Beckmann |
| 10,594,956 | B2 | 3/2020 | Holmes |
| 10,676,794 | B2 | 6/2020 | Amini |
| 2001/0045449 | A1 | 11/2001 | Shannon |
| 2002/0119513 | A1 | 8/2002 | Alocilja |
| 2003/0088442 | A1 | 5/2003 | Michael |
| 2003/0214387 | A1 | 11/2003 | Giaccherini |
| 2004/0018641 | A1 * | 1/2004 | Goldsmith ............... C12Q 1/22 436/518 |
| 2004/0069046 | A1 | 4/2004 | Sunshine |
| 2004/0074957 | A1 | 4/2004 | Devar |
| 2004/0148117 | A1 | 7/2004 | Kirshenbaum |
| 2004/0154739 | A1 | 8/2004 | Shanahan |
| 2004/0204881 | A1 | 10/2004 | Mayer |
| 2004/0226392 | A1 | 11/2004 | McNally |
| 2005/0060246 | A1 | 3/2005 | Lastinger |
| 2005/0061877 | A1 | 3/2005 | Stevens |
| 2005/0104730 | A1 | 5/2005 | Yang |
| 2005/0144027 | A1 * | 6/2005 | Brunner ............... B65D 33/004 705/1.1 |
| 2005/0149470 | A1 | 7/2005 | Fujie |
| 2005/0197912 | A1 | 9/2005 | Wittmer |
| 2005/0203790 | A1 | 9/2005 | Cohen |
| 2005/0222889 | A1 | 10/2005 | Lai |
| 2005/0228712 | A1 | 10/2005 | Bornstein |
| 2006/0006987 | A1 | 1/2006 | Hashimoto |
| 2006/0071774 | A1 | 4/2006 | Brown |
| 2006/0080819 | A1 | 4/2006 | McAllister |
| 2006/0097875 | A1 | 5/2006 | Ott |
| 2006/0238307 | A1 | 10/2006 | Bauer |
| 2006/0244718 | A1 | 11/2006 | Hiddink |
| 2007/0050070 | A1 | 3/2007 | Strain |
| 2007/0050271 | A1 | 3/2007 | Ufford |
| 2007/0064765 | A1 | 3/2007 | Solie |
| 2007/0067177 | A1 | 3/2007 | Martin |
| 2007/0067203 | A1 | 3/2007 | Gil |
| 2007/0069867 | A1 | 3/2007 | Fleisch |
| 2007/0076779 | A1 | 4/2007 | Haarer |
| 2007/0156261 | A1 | 7/2007 | Caldwell |
| 2007/0176773 | A1 | 8/2007 | Smolander |
| 2007/0221727 | A1 | 9/2007 | Reznik |
| 2008/0001752 | A1 | 1/2008 | Bruns |
| 2008/0052201 | A1 | 2/2008 | Bodin |

(56) References Cited

U.S. PATENT DOCUMENTS

| | | |
|---|---|---|
| 2008/0067227 A1 | 3/2008 | Poss |
| 2008/0073431 A1* | 3/2008 | Davis ............... G06F 3/147 |
| | | 235/383 |
| 2008/0103944 A1 | 5/2008 | Hagemann |
| 2008/0186175 A1 | 8/2008 | Stern |
| 2008/0292759 A1 | 11/2008 | Palmer |
| 2008/0294488 A1 | 11/2008 | Gupta |
| 2009/0027213 A1 | 1/2009 | Debord |
| 2009/0040063 A1 | 2/2009 | Yearsley |
| 2009/0058644 A1 | 3/2009 | French |
| 2009/0076645 A1 | 3/2009 | Ben-Tzur |
| 2009/0083054 A1 | 3/2009 | Koo |
| 2009/0144122 A1 | 6/2009 | Ginsberg |
| 2009/0261974 A1 | 10/2009 | Bailey |
| 2009/0322481 A1* | 12/2009 | Marr, III ............. H04Q 9/00 |
| | | 340/10.1 |
| 2010/0006646 A1 | 1/2010 | Stiller |
| 2010/0007464 A1 | 1/2010 | McTigue |
| 2010/0042369 A1 | 2/2010 | Mian |
| 2010/0065632 A1* | 3/2010 | Babcock ............. G06Q 10/08 |
| | | 235/385 |
| 2010/0101317 A1 | 4/2010 | Ashrafzadeh |
| 2010/0138281 A1 | 6/2010 | Zhang |
| 2011/0029413 A1 | 2/2011 | Ben-Tzur |
| 2011/0035326 A1 | 2/2011 | Sholl |
| 2011/0068921 A1 | 3/2011 | Shafer |
| 2011/0301903 A1 | 12/2011 | Humbert |
| 2012/0101876 A1 | 4/2012 | Turvey |
| 2012/0161967 A1 | 6/2012 | Stern |
| 2012/0264446 A1 | 10/2012 | Xie |
| 2012/0267541 A1 | 10/2012 | Utukuri |
| 2012/0304014 A1 | 11/2012 | Prophete |
| 2012/0310853 A1 | 12/2012 | Aldstadt |
| 2013/0117053 A2 | 5/2013 | Campbell |
| 2013/0176115 A1 | 7/2013 | Puleston |
| 2013/0214797 A1 | 8/2013 | Gruden |
| 2013/0218511 A1 | 8/2013 | Mager |
| 2013/0235206 A1 | 9/2013 | Smith |
| 2013/0282522 A1 | 10/2013 | Hassan |
| 2014/0138440 A1 | 5/2014 | D'Ambrosio |
| 2014/0180953 A1 | 6/2014 | Westcott |
| 2014/0201041 A1 | 7/2014 | Meyer |
| 2014/0208779 A1* | 7/2014 | Bell .................. A47F 3/0482 |
| | | 62/62 |
| 2014/0297487 A1 | 10/2014 | Bashkin |
| 2014/0313055 A1* | 10/2014 | Warkentin .......... H04Q 9/00 |
| | | 340/870.16 |
| 2014/0316875 A1 | 10/2014 | Tkachenko |
| 2014/0330407 A1 | 11/2014 | Corder |
| 2015/0015373 A1 | 1/2015 | Mongrenier |
| 2015/0021401 A1 | 1/2015 | Rajagopal |
| 2015/0022313 A1 | 1/2015 | Maier |
| 2015/0041616 A1 | 2/2015 | Gentile |
| 2015/0048938 A1 | 2/2015 | Tew |
| 2015/0084100 A1* | 3/2015 | Sablong ............. G01N 27/126 |
| | | 257/253 |
| 2015/0186840 A1 | 7/2015 | Torres |
| 2015/0192475 A1 | 7/2015 | Eisenstadt |
| 2015/0338846 A1 | 11/2015 | Boivin |
| 2015/0347945 A1 | 12/2015 | Reese |
| 2016/0012337 A1 | 1/2016 | Kaye |
| 2016/0026032 A1 | 1/2016 | Moore |
| 2016/0034907 A1 | 2/2016 | Worrall |
| 2016/0048798 A1 | 2/2016 | Meyer |
| 2016/0063367 A1 | 3/2016 | Cai |
| 2016/0132821 A1 | 5/2016 | Glasgow |
| 2016/0189087 A1 | 6/2016 | Morton |
| 2016/0203591 A1 | 7/2016 | Justaniah |
| 2016/0217417 A1 | 7/2016 | Ma |
| 2016/0239794 A9 | 8/2016 | Shafer |
| 2016/0283904 A1 | 9/2016 | Siegel |
| 2016/0292634 A1 | 10/2016 | Mehring |
| 2016/0300285 A1* | 10/2016 | Gandhi ............. G06Q 30/0623 |
| 2016/0307040 A1 | 10/2016 | Shulman |
| 2016/0314514 A1 | 10/2016 | High |
| 2016/0350715 A1 | 12/2016 | Minvielle |
| 2017/0039194 A1 | 2/2017 | Tschetter |
| 2017/0039511 A1* | 2/2017 | Corona ............. G06K 9/6267 |
| 2017/0059391 A1 | 3/2017 | Ademe |
| 2017/0074921 A1 | 3/2017 | Uota |
| 2017/0102694 A1 | 4/2017 | Enver |
| 2017/0116565 A1 | 4/2017 | Feiner |
| 2017/0122771 A1 | 5/2017 | Keal |
| 2017/0164773 A1 | 6/2017 | Wirtz |
| 2017/0255901 A1 | 9/2017 | Bermudez Rodriguez |
| 2017/0269601 A1 | 9/2017 | Jones |
| 2017/0286905 A1 | 10/2017 | Richardson |
| 2017/0300984 A1 | 10/2017 | Hurwich |
| 2017/0322090 A1 | 11/2017 | Jones |
| 2017/0344934 A1 | 11/2017 | Millhouse |
| 2017/0344935 A1 | 11/2017 | Mattingly |
| 2018/0007453 A1 | 1/2018 | Taylor |
| 2018/0045700 A1 | 2/2018 | Biermann |
| 2018/0078992 A1 | 3/2018 | High |
| 2018/0096175 A1 | 4/2018 | Schmeling |
| 2018/0143131 A1 | 5/2018 | Choi |
| 2018/0144430 A1 | 5/2018 | Millhouse |
| 2018/0180492 A1 | 6/2018 | Ribi |
| 2018/0195869 A1 | 7/2018 | High |
| 2018/0211208 A1 | 7/2018 | Winkle |
| 2018/0217118 A1 | 8/2018 | Payne |
| 2018/0242768 A1 | 8/2018 | Lewis |
| 2018/0247257 A1 | 8/2018 | Lert, Jr. |
| 2018/0270631 A1 | 9/2018 | High |
| 2018/0290809 A1 | 10/2018 | Espinosa |
| 2018/0341905 A1 | 11/2018 | Johnsen |
| 2019/0147396 A1 | 5/2019 | Bohling |
| 2019/0223643 A1 | 7/2019 | Hara |
| 2019/0285603 A1 | 9/2019 | Velez |
| 2020/0118072 A1 | 4/2020 | Johnson |

FOREIGN PATENT DOCUMENTS

| | | |
|---|---|---|
| CN | 201314907 | 9/2009 |
| CN | 202306566 U | 7/2012 |
| CN | 102930649 | 2/2013 |
| CN | 203275285 | 11/2013 |
| CN | 203306566 | 11/2013 |
| CN | 103543703 A | 1/2014 |
| CN | 103593746 | 2/2014 |
| CN | 104036354 | 9/2014 |
| CN | 204010264 | 12/2014 |
| CN | 104749329 | 7/2015 |
| CN | 204514846 | 7/2015 |
| CN | 105444504 | 3/2016 |
| CN | 106408173 | 2/2017 |
| CN | 106600286 | 4/2017 |
| CN | 107703269 | 2/2018 |
| EP | 1221613 | 7/2002 |
| EP | 1374688 A1 | 1/2004 |
| EP | 2165298 A1 | 3/2010 |
| EP | 2509412 | 10/2012 |
| EP | 2509412 A1 | 10/2012 |
| EP | 2835078 | 2/2015 |
| JP | 2002195971 A | 7/2002 |
| JP | 2008004133 | 1/2008 |
| JP | 2008004133 A | 1/2008 |
| JP | 2013068547 | 4/2013 |
| WO | 2000078919 A1 | 12/2000 |
| WO | 2001023256 | 4/2001 |
| WO | 2003098175 | 11/2003 |
| WO | 2007052208 A1 | 5/2007 |
| WO | 2008006152 A1 | 1/2008 |
| WO | 2012125960 | 9/2012 |
| WO | 2013174983 | 11/2013 |
| WO | 2014059048 | 4/2014 |

(56) References Cited

FOREIGN PATENT DOCUMENTS

| WO | 2015061429 | 4/2015 |
|---|---|---|
| WO | 2015066594 | 5/2015 |

OTHER PUBLICATIONS

U.S. Appl. No. 16/112,974, filed Aug. 27, 2018, Joshua Bohling.
Bedard, Jean; "Temperature Mapping of Storage Areas"; Technical supplement to WHO Technical Report Series, No. 961, 2011; WHO Press, World Health Organization; available at least as early as Jan. 2014; pp. 1-25.
compact.net; "Inspection Planning / Quality Inspection / SPC / LIMS"; https://www.caq.de/en/Software/InspectionPlanning_QualityInspection_SPC; available at least as early as Jan. 27, 2017; pp. 1-4.
Greis, Noel P.; "Monitoring the 'Cool Chain' Maximizing Shelf Life for Safer Food"; https://atecentral.net/r20093/case_study_monitoring_the_cool_chain; National Science Foundation; published on Dec. 2011; pp. 1-9.
IQA Team; "Material Inspection Using a Cloud Software"; http://Mqalims.com/wp-content/uploads/2015/02/MAT_INSP.pdf; available at least as early as Jan. 27, 2017; pp. 1-5.
Jedermann, Reiner, et al.; "Semi-passive RFID and Beyond: Steps Towards Automated Quality Tracing in the Food Chain"; Inderscience Enterprises Ltd.; Int. J. Radio Frequency Identification Technology and Applications, vol. 1, No. 3; published in 2007; pp. 247-259.
MIPSIS; "Quality Control Inspection Software"; http://www.mipsis.com/QualityInspectionSoftware.html; available at least as early as Jan. 27, 2017; pp. 1-3.
Moorthy, Rahul, et al.; "On-Shelf Availability in Retailing"; vol. 116—No. 23; International Journal of Computer Applications; available at least as early as Apr. 2015; pp. 47-51.
QC One; "Inspect. Report. Analyze. Quality Control Software for Fresh Produce"; http://qcone.com/en/; available at least as early as May 29, 2017; pp. 1-2.
Ryan, John M.; "Guide to Food Safety and Quality During Transportation: Controls, Standards and Practices"; Academic Press; available at least as early as 2014; pp. 1-8.
Softexpert; "SE Inspection Incoming/Outgoing Goods Inspection and Supplier Management"; https://softexpert.com/inspection-evaluation-goods.php; available at least as early as Jan. 27, 2017; pp. 1-3.
Yan, Lu, et al.; "The Internet of Things: From RFID to the Next-Generation Pervasive Networked Systems"; Auerbach Publications; New York; available at least as early as 2008; pp. 1-35.
Eom, Ki-Hwan, et al.; "The Meat Freshness Monitoring System Using the Smart RFID Tag", International Journal of Distributed Sensor Networks, vol. 2014, Jul. 9, 2014, http://journals.sagepub.com/doi/10.1155/2014/591812, pp. 1-10.
PCT; App. No. PCT/US2015/067902; International Search Report and Written Opinion dated Mar. 29, 2016.
U.S. Appl. No. 15/541,160; Notice of Allowance dated Feb. 26, 2018; (pp. 1-8).
U.S. Appl. No. 15/922,090, dated Mar. 15, 2018, High, Donald.
U.S. Appl. No. 15/874,366, dated Jan. 18, 2018, Winkle, David.
Moorthy, Rahul et al.; "On-Shelf Availability in Retailing"; vol. 116—No. 23; International Journal of Computer Applications; Apr. 2015; pp. 47-51.
BT9 Intelligent Supply Chain Solutions; "Multi Segment, Real Time, Cold Chain Perishable Information"; http://www.bt9-tech.com; Published 2018; pp. 1-6.
Marvin, Rob; "Blockchain: The Invisible Technology That's Changing the World"; https://in.pcmag.com/amazon-web-services/112363/blockchain-the-invisible-technology-thats-changing-the-world; Aug. 30, 2017; pp. 1-29.
Food and Agriculture Organization of the United Nations; "Flying robots for food security"; http://www.fao.org/zhc/detail-events/en/c/428256; Aug. 10, 2016; pp. 1-3.
Ahearn, Brianna; "Kroger Wins for Food Temperature Innovation"; https://www.retailsupplychaininsights.com/doc/kroger-wins-for-food-temperature-innovation-0001; Jun. 4, 2015; pp. 1-2.
DJI Ferntech; "Drones for Agriculture"; https://www.djistore.co.nz/agriculture; Available at least as early as Feb. 7, 2019; pp. 1-13.
Hagen, Christian et al.; "A Fresh Look: Perishable Supply Chains Go Digital"; https://www.atkearney.com/operations-performance-transformation/article?/a/a-fresh-look-perishable-supply-chains-go-digital; Available at least as early as Feb. 7, 2019; pp. 1-22.
Friedman, Phil; "AI, machine learning, and more efficient routing"; https://www.omnitracs.com/blog/ai-machine-learning-and-more-efficient-routing; Jun. 28, 2018; pp. 1-6.
Pridevel; "IoT Cold Chain Monitoring"; http://www.pridevel.com/sap-iot-cold-chain-monitoring; Available at least as early as Feb. 7, 2019; pp. 1-3.
Mazur, Michal; "Six Ways Drones Are Revolutionizing Agriculture"; https://www.technologyreview.com/s/601935/six-ways-drones-are-revolutionizing-agriculture; Jul. 20, 2016; pp. 1-5.
Sensefly; "Why Use Agriculture Drones?"; https://www.sensefly.com/industry/agricultural-drones-industry; Available at least as early as Feb. 7, 2019; pp. 1-15.
Smilo; "The latest generation hybrid blockchain platform"; https://smilo.io/files/Smilo_White_Paper V1.8.1.pdf; Available at least as early as Feb. 7, 2019; pp. 1-33.
Tive; "A Complete Supply Chain Visibility System"; https://tive.co/product; Available at least as early as Feb. 7, 2019; pp. 1-7.
Intel; "Intelligent Dynamic Store Merchandising Solution Cuts Losses on Perishables and Raises Brand Awareness"; Available at least as early as Feb. 7, 2019; pp. 1-12.
Tsenso; "The Fresh Index: A Real-Time Shelf Life Indicator"; https://tsenso.com/en/freshindex-instead-of-bestbefore; Available at least as early as Feb. 7, 2019; pp. 1-5.
Musani, Parvez; "Eden: the Tech That's Bringing Fresher Groceries to You"; https://blog.walmart.com/innovation/20180301/eden-the-tech-thats-bringing-fresher-groceries-to-you; Mar. 1, 2018; pp. 1-4.
Husseini, Talal; "Walmart's 'Eden' artificial intelligence technology to inspect fresh food for spoilage"; https://www.foodprocessing-technology.com/news/walmarts-eden-artificial-intelligence-technology-inspect-fresh-food-spoilage; Mar. 2, 2018; pp. 1-4.
Peterson, Hayley; "Walmart is saving $2 billion with a machine called 'Eden' that inspects food and knows when it will spoil"; https://www.businessinsiderin/walmart-is-saving-2-billion-with-a-machine-called-eden-that-inspects-food-and-knows-when-it-will-spoil/articleshow/63127641.cms; Mar. 1, 2018; pp. 1-12.
Xinfin; "Enterprise Ready Hybrid Blockchain for Global Trade and Finance"; https://www.xinfin.org; Available at least as early as Feb. 7, 2019; pp. 1-13.
Freshfruitportal.Com; "Zest Labs fights food waste by routing pallets according to real-time freshness"; https://www.freshfruitportaI.com/news/2018/07/19/technology-zest-labs-food-waste-profits-sensors; Jul. 19, 2018; pp. 1-5.
Smart Sense; "Supermarket Remote Monitoring Solutions"; https://www.smartsense.co/industries/retail/supermarkets; Available at least as early as Feb 7, 2019; pp. 1-6.
Fast Casual; "Wireless temperature-monitoring, tracking solution available for shipping perishable goods"; https://www.fastcasual.com/news/wireless-temperature-monitoring-and-tracking-solution-now-available-for-shipping-perishable-goods/; Aug. 15, 2017; pp. 1-10.
3M; "3M MonitorMark Time Temperature Indicators"; https://www.3m.com/3M/en_US/company-us/all-3m-products/~/Monmark-3M-MonitorMark-Time-Temperature-Indicators/?N=5002385+3293785721&rt=rud; Available at least as early as Feb. 7, 2019; pp. 1-4.
Tech Mahindra; "Cold Chain Monitoring"; https://www.techmahindra.com/services/NextGenSolutions/Des/Solutions/Cold_Chain_Monitoring.aspx; Available at least as early as Feb. 7, 2019; pp. 1-4.
Tech Mahindra; "Farm to fork"; https://www.techmahindra.com/services/NextGenSolutions/Des/ Solutions/Farm_to_fork.aspx; Available at least as early as Feb. 7, 2019; pp. 1-2.
Impact Vision; "Non-invasive, real time food quality information"; https://www.impactvi.com/; Available at least as early as Feb. 7, 2019; pp. 1-18.

(56) References Cited

OTHER PUBLICATIONS

Sensegrow; "Supply Chain Monitoring with Real-time IoT Platform"; http://www.sensegrow.com/blog/supply-chain-monitoring; May 10, 2018; pp. 1-5.
De Troch, Stefan; "Item-level cold chain monitoring, another cool NFC solution"; https://blog.nxp.com/internet-of-things-2/item-level-cold-chain-monitoring-another-cool-nfc-solution; Aug. 30, 2016; pp. 1-5.
Tive; "Environmental Monitoring for Perishables"; https://tive.co/solution/environmental-monitoring-for-perishables/; Available at least as early as Feb. 7, 2019; pp. 1-5.
Springer, Jon; "Walmart, Kroger join suppliers in blockchain food safety initiative"; https://www.supermarketnews.com/news/walmart-kroger-join-suppliers-blockchain-food-safety-initiative; Aug. 22, 2017; pp. 1-4.
Business Wire; "Emerson Expands Global Capabilities in Fresh Food Monitoring with Acquisitions of Locus Traxx and PakSense"; https://www.businesswire.com/news/home/20160830005136/en/Emerson-Expands-Global-Capabilities-Fresh-Food-Monitoring; Aug. 30, 2016; pp. 1-2.
Digi; "Digi Honeycomb Keeping food safe just got easier and cheaper. Digi Honeycomb lets you monitor your entire Cold Chain System"; https://s3.amazonaws.com/telusdigital-marketplace-production/iot/user-content/product/64aa-o.pdf; Available at least as early as Feb. 7, 2019; pp. 1-2.
Harvard Business Review; "How Blockchain Will Accelerate Business Performance and Power the Smart Economy"; https://hbrorg/sponsored/2017/10/how-blockchain-will-accelerate-business-performance-and-power-the-smart-economy; Oct. 27, 2017; pp. 1-8.
Ambrosus; "Decentralised IoT Networs for Next-Generation Supply Chains"; https://ambrosus.com/#home; Available at least as early as Feb. 7, 2019; pp. 1-12.
IBM; "Take your food data further with Fresh Insights for IBM Food Trust"; https://www.ibm.com/blockchain/solutions/food-trust/freshness; Available at least as early as Feb. 7, 2019; pp. 1-3.
Palanza, Rich; "IoT Monitoring: Rapidly Deliver on the Promise of IoT"; https://business.weather.com/blog/iot-monitoring-rapidly-deliver-on-the-promise-of-iot; May 16, 2018; pp. 1-4.
Zest Labs; "Zest Fresh for Growers, Retailers and Restaurants"; https://www.zestlabs.com/zest-fresh-for-produce/; Available at least as early as Feb. 7, 2019; pp. 1-7.
Emerson; "ProAct Services and ProAct Transport"; https://www.emerson.com/en-us/commercial-residential/proact; Available at least as early as Feb. 7, 2019; pp. 1-4.
Emerson; "Real-Time Temperature & Location Trackers"; https://climate.emerson.com/en-us/products/controls-monitoring-systems/cargo-tracking-nrionitoring/trackers; Available at least as early as Feb. 7, 2019; pp. 1-4.
Emerson; "Supply Chain Data Loggers"; https://climate.emerson.com/en-us/products/controls-monitoring-systems/cargo-tracking-monitoring/loggers; Available at least as early as Feb. 7, 2019; pp. 1-4.
Infratab; "Products"; https://infratab.com/products/; Available at least as early as Feb. 7, 2019; pp. 1-2.
Oracle; "Oracle Unveils Business-Ready Blockchain Applications"; https://www.oracle.com/nz/corporate/pressrelease/oow18-oracle-blockchain-applications-cloud-2018-10-23.html; Oct. 23, 2018; pp. 1-4.
Agrofresh; "FreshCloud Tm Storage Insights helps you monitor fruit in storage for added peace of mind"; https://www.agrofresh.com/technologies/freshcloud/storage-insights/; Available at least as early as Feb. 7, 2019; pp. 1-4.
Verigo; "Introducing Pod Quality Continuous Product Life Data, From Farm to Store"; https://www.farmtoforkfresh.com/; Available at least as early as Feb. 7, 2019; pp. 1-8.
TCS Worldwide; "TCS Cargo Monitoring Solution: Track freshness of perishable cargo"; https://www.tcs.com/cargo-monitoring-solution; Available at least as early as Feb. 7, 2019; pp. 1-7.
Cao, Jordan; "Intelligent Container—powered by SAP HANA"; https://blogs.saphana.com/2018/09/27/intelligent-container-powered-sap-hana/; Sep. 27, 2018; pp. 1-5.
Grand View Research; "Cold Chain Market Size Worth $447.50 Billion by 2025 | Cagr: 15.1%"; https://www.grandviewresearch.com/press-release/global-cold-chain-market; Mar. 2019; pp. 1-10.
Yiannas, Frank; "How Walmart's Spark Keeps Your Food Fresh"; https://blog.walmart.com/sustainability/20150112/how-walmarts-spark-keeps-your-food-fresh; Jan. 12, 2015; pp. 1-16.
Ripple News Tech Staff; "Alibaba is Using Blockchain to Improve Consumer Confidence and Fight Food Fraud"; https://ripplenews.tech/2018/05/03/alibaba-is-using-blockchain-to-improve-consumer-confidence-and-fight-food-fraud/; May 3, 2018; pp. 1-7.
Hsu, Jenny W.; "Freshippo Customers Can Track Farm-To-Shelf Journey for Food"; https://www.alizila.com/hema-food-tracking/; Aug. 7, 2018; pp. 1-6.
Impinj; "Hy-Vee Grocery Automates Cold Chain Monitoring"; https://www.impinj.com/library/customer-stories/hy-vee-cold-chain-monitoring-increases-shelf-life/; Available as early as Feb. 7, 2019; pp. 1-3.
Freshai; "AI-powered waste reduction for smart food businesses."; http://freshai.farmsteadapp.com/; Available as early as Feb. 7, 2019; pp. 1-5.
Wynne-Jones, Stephen; "Maxima Group Unveils 'Electronic Nose' to Track Freshness"; https://www.esmmagazine.com/maxima-group-unveils-elecrtronic-nose-track-freshness/29589; Jul. 5, 2016; pp. 1-4.
Carrefour Group; "Carrefour launches Europe's first food blockchain"; http://www.carrefour.com/current-news/carrefour-launches-europes-first-food-blockchain; Mar. 6, 2018; pp. 1-2.
Gabbett, Rita Jane; "Amazon using artificial intelligence to monitor food safety issues"; http://www.micausa.org/amazon-using-artificial-intelligence-monitor-food-safety-issues/; May 9, 2018; pp. 1-3.
Traqtion; "TraQtion's Supply Chain Solution Manages Global Food Supplier Compliance and Audits"; https://www.traqtion.com/documents/TraQtion-Costco.pdf; Available as early as Feb. 7, 2019; pp. 1-2.
Ecoark Holdings, Inc.; "Ocean Mist Farms Selects Zest Fresh to Optimize Freshness Management"; https://www.globenewswire.com/news-release/2018/12/04/1661680/0/en/Ocean-Mist-Farms-Selects-Zest-Fresh-to-Optimize-Freshness-Management.html; Dec. 4, 2018; pp. 1-3.
My Devices; "Alibaba Cloud and myDevices Partner to Launch Turnkey IoT Solutions in China"; https://mydevices.com/newspost/alibaba-cloud-mydevices-partner-launch-turnkey-iot-solutions-china/; Sep. 11, 2018; pp. 1-3.
Qa; "Carrefour and SGS Launch Visual Trust in China"; https://www.qualityassurancemag.com/article/carrefour-and-sgs-launch-visual-trust-in-china/; Sep. 28, 2017; pp. 1-4.
TE-Food; "TE-Food Partners with Halal Trail Bringing Halal Food Companies to the Blockchain"; https://www.reuters.com/brandfeatures/venture-capital/article?id=38153; May 31, 2018; pp. 1-6.
Kroger; "Kroger Gets HarvestMark Allows consumers to trace the origin of salads"; https://www.cspdailynews.com/foodservice/kroger-gets-harvestmark; Oct. 29, 2009; pp. 1-11.
Trimble; "Trimble Acquires HarvestMark to Provide Food Traceability and Quality Control"; https://www.prnewswire.com/news-releases/trimble-acquires-harvestmark-to-provide-food-traceability-and-quality-control-300070050.html; Apr. 22, 2015; pp. 1-6.
Wageningen UR Food & Biobased Research; "Food & Biobased Research"; https://www.worldfoodinnovations.com/userfiles/documents/Fbr%20Corporate%20Brochure.pdf; Jul. 2014; pp. 1-24.
Whelan, Jenny; "Kelsius to Install FoodCheck Monitoring System in SuperValu and Centra Stores"; https://www.checkout.ie/kelsius-signs-deal-to-put-foodcheck-monitoring-system-in-supervalu-and-centra-stores/; Aug. 6, 2015; pp. 1-4.
Greenwalt, Megan; "Acquisition Leads to New, Fresh Food Waste Solution"; https://www.waste360.com/mergers-and-acquisitions/acquisition-leads-new-fresh-food-waste-solution; Aug. 15, 2018; pp. 1-6.
Anzilotti, Eillie; "These High-Tech Sensors Track Exactly How Fresh Our Produce Is So We Stop Wasting Food"; https://www.

(56) References Cited

OTHER PUBLICATIONS fastcompany.com/40424163/these-high-tech-sensors-track-exactly-how-fresh-our-produce-is-so-we-stop-wasting-food; May 26, 2017; pp. 1-3.
Teijin—Human Chemistry, Human Solutions, Teijin's RFID Smart Shelf-Management System Used for Mass Document Management. Retrieved online at: http://www.teijin.com/news/2014/ ebd140307_11.html. 2 pages, Mar. 7, 2014.
The NeWave® Smart Inventory Managment System: Take Your Management to the Next Level, NeWave Sensor Solutions Innovation Center, Oct. 7, 2016; pp. 1-2.
Arah, Isaac Kojo et al.; "Preharvest and Postharvest Factors Affecting the Quality and Shelf Life of Harvested Tomatoes: A Mini Review"; http://downloads.hindawi.com/journals/ija/2015/478041.pdf; Available as early as Oct. 14, 2015; pp. 1-7.
Badia, Ricardo; "Cold Chain Logistics: Assessing the Challenge"; https://www.zestlabs.com/assessing-cold-chain-logistics/; Mar. 19, 2019; pp. 1-4.
Barthe, J.F.; "D.2.3.2. Database of consumer awareness, expectations and concerns on cold chain"; http://www.frisbee-project.eu/images/result/FRISBEE_DEL_2-3-2.pdf; Dec. 2, 2011; pp. 1-26.
Barthe, J.F.; "D.2.3.2.1 Survey questionnaires and materials for studies of consumer perspectives and attitudes towards refrigerated foods, the cold chain and relevant refrigeration technologies (Informed consent forms, privacy, personal data handling)"; http://www.frisbee-project.eu/images/result/FRISBEE_DEL_2-3-2-1.pdf;Feb. 8, 2012; pp. 1-21.
Bevan et al.; "Storage of Organically Produced Crops"; https://orgprints.org/8241/1/Storage_organic_produce_report.pdf; Dec. 1997; pp. 1-227.
Bogataj, M., et al.; "Stability of perishable goods in cold logistic chains"; International Journal of Production Economics, vol. 93-94; 2005; pp. 345-356.
U.S. Appl. No. 16/526,677, dated Jul. 30, 2019, Bohling, Joshua.
Capgemini; "Schuitema Revolutionizes Food Quality Control Through RFID"; https://www.capgemini.com/se-en/wp-content/uploads/sites/29/2017/07/Schuitema_R evolutionizes_Food_Quality_Control_Through_RFID.pdf; Jul. 29, 2017; pp. 1-2.
Chainlink Research; "Achieving Consistent Product Quality"; https://www.zestlabs.com/wp-content/uploads/2016/12/Quality-Management-For-Produce.pdf; Available as early as Dec. 2016; pp. 1-8.
Chainlink Research; "Measuring Produce Freshness: The Key to Preventing Waste"; https://www.zestlabs.com/wp-content/uploads/2016/03/Measuring-Produce-Freshness.pdf; Available as early as Mar. 2016; pp. 1-12.
Chainlink Research; "Preemptive Freshness Management"; https://www.zestlabs.com/wp-content/uploads/2017/03/Preemptive-Freshness-Management.pdf; Available as early as Mar. 2017; pp. 1-8.
Chainlink Research; "Blockchain's Role in the Produce Supply Chain"; https://www.zestlabs.com/wp-content/uploads/2018/01/Blockchains-Role-in-the-Prod uce-Supply-Chain.pdf; Available as early as Jan. 2018; pp. 1-20.
Chainlink Research; "Pallet-level Monitoring"; https://www.zestlabs.com/wp-content/uploads/2016/03/Pallet-Monitoring-for-the-Fresh-Food-Supply-Chain.pdf; Available as early as Mar. 2016; pp. 1-9.
Chainlink Research; "Why Quality Consistency Matters"; https://www.zestlabs.com/wp-content/uploads/2016/03/Why-Food-Supply-Chain-Quality-Matters-1.pdf; Available as early as Mar. 2016; pp. 1-10.
Claussen, Ingrid C.; "Deliverable D.3.2.4.3 Literature review and experimental data of chilled, superchilled/supercooled fish quality and safety models"; http://www.frisbee-project.eu/images/result/ FRISBEE_DEL_3-2-4-3.pdf; May 6, 2011; pp. 1-29.
Colmer, Christian; "Chill—On! Transparent food quality all the way"; https://www.innovations-report.com/html/reports/medicine-health/chill-transparen Wood-quality-168201.html; Oct. 1, 2011; pp. 1-5.
Cotillon, C.; "Deliverable 8.2.1.1 Publication in Scientific Journals"; http://www.frisbee-project.eu/images/result/FRISBEE_DEL_8.2.1.1.pdf; Oct. 27, 2011; pp. 1-5.
Cotillon, C.; "Deliverable 8.3.3.1 Mini conferences"; http://www.frisbee-project.eu/images/result/FRISBEE_DEL_8.3.3.1.pdf; Dec. 7, 2011; pp. 1-8.
Cotillon, C.; "Deliverable 8.6.1 Report on collaboration with other EU projects"; http://www.frisbee-project.eu/images/result/FRISBEE_DEL_8.6.1.pdf; Dec. 5, 2011; pp. 1-12.
Dada, Ali, et al.; "Sensor Applications in the Supply Chain: The Example of Quality-Based Issuing of Perishables"; The Internet of Things. Lecture Notes in Computer Science, edited by Christian Floerkemeier, et al.; vol. 4952; 2008; pp. 140-154.
Desmedt, Frederique; "Deliverable 8.1.1 Project logo, Leaflet and PowerPoint presentation"; http://www.frisbee-project.eu/images/result/FRISBEE_DEL_8.1.1.pdf; Nov. 19, 2010; pp. 1-30.
Desmedt, Frederique; "Deliverable 8.1.2 Project internet and intranet website"; http://www.frisbee-project.eu/images/result/FRISBEE_DEL_8.1.2.pdf; Mar. 3, 2011; pp. 1-9.
Do Nascimento Nunes, M. C., et al.; "Improvement in fresh fruit and vegetable logistics quality: berry logistics field studies"; Philosophical Transactions of the Royal Society; http://dx.doi.org/10.1098/rsta.2013.0307; 2014; pp. 1-19.
Doyle, John P.; "Seafood Shelf Life as a Function of Temperature"; Alaska Sea Grant Marine Advisory Program; No. 30; 1989; pp. 1-6.
Evans, J.; "Deliverable D2.2.2 : Assessment of current refrigeration technologies of selected food industries and their potential improvement in current refrigeration"; http://www.frisbee-project.eu/images/result/FRISBEE_DEL_2-2-2.pdf; Jan. 30, 2012; pp. 1-181.
Evans, Judith et al.; "Deliverable D.2.2.3 : Analysis of potential of novel refrigeration technologies suitable for selected industries for application and improvement of food quality, energy consumption and environmental impact"; http://www.frisbee-project.eu/images/result/FRISBEE_DEL_2-2-3.pdf; Dec. 2, 2011; pp. 1-54.
Friedlos, Dave; "New Zealand Kiwifruit Processor Finds ROI"; https://www.rfidjournal.com/articles/view?4090; May 20, 2008; pp. 1-4.
Frisbee; "Frisbee european project—Archive"; https://web.archive.org/web/20180815100417/http://www.frisbee-project.eu/archive-results.html; Available as early as Aug. 15, 2018; pp. 1-5.
Frisbee; "Frisbee european project—Developing novel breakthrough technologies"; https://web.archive.org/web/20180316101206/http://www.frisbee-project.eu/researc h/92-developing-novel-breakthrough-technologies.html; Available as early Mar. 16, 2018; pp. 1-3.
Frisbee; "Frisbee european project—Frisbee at the Sixteenth Conference on Food Microbiology, Belgium"; http://www.frisbee-project.eu/news/40-frisbee-at-the-sixteenth-conference-on-food-microbiology.html; Nov. 15, 2011; pp. 1-1.
Frisbee; "Frisbee european project—Frisbee develops a Virtual Platform application"; http://www.frisbee-project.eu/news/90-frisbee-develops-a-virtual-platform-application.html; Mar. 18, 2013; pp. 1-1.
Frisbee; "Frisbee european project—Frisbee dissemination activities"; http://www.frisbee-project.eu/news/91-frisbee-dissemination-activities.html; Mar. 18, 2013; pp. 1-1.
Frisbee; "Frisbee european project—Frisbee on the starting-blocks"; http://www.frisbee-project.eu/news/49-frisbee-on-the-starting-blocks.html; Mar. 9, 2012; pp. 1-2.
Frisbee; "Frisbee european project—Frisbee welcomes New Members Advisory Board"; http://www.frisbee-project.eu/news/48-new-members-advisory-board.html; Mar. 9, 2012; pp. 1-1.
Frisbee; "Frisbee european project—Frisbee: Latest Developments"; http://www.frisbee-project.eu/news/42-frisbee-project-latest-developments.html; Dec. 21, 2011; pp. 1-2.
Frisbee; "Frisbee european project—Join the first European Food Cold Chain Database!!!";http://www.frisbee-project.eu/news/55-database2.html; Jul. 9, 2012; pp. 1-2.
Frisbee; "Frisbee european project—Magnetic refrigeration technology. Frisbee's experts team work on this disruptive technology"; https://web.archive.org/web/20180316101206/http://www.frisbee-project.eu/research/51-magnetic-refrigeration-technology.html; Available as early as Mar. 16, 2018; pp. 1-3.
Frisbee; "Frisbee european project—MEP-scientist pairing scheme"; http://www.frisbee-project.eu/news/41-mep-scientist-pairing-scheme.html; Dec. 20, 2011; pp. 1-2.

(56) References Cited

OTHER PUBLICATIONS

Frisbee; "Frisbee european project—Nanoparticles, a concentrate of energy: PCM nanoparticles where low temperatures are needed"; https://web.archive.org/web/20180316101206/http://www.frisbee-project.eu/research/27-nanoparticles-a-concentrate-of-energy.html; Available as early as Mar. 16, 2018; pp. 1-2.

Frisbee; "Frisbee european project—Project Overview"; https://web.archive.org/web/20120211082956/http://www.frisbee-project.eu/project-overview.html; Available as early as Feb. 11, 2012; pp. 1-1.

Frisbee; "Frisbee european project—Saving energy by refrigeration predictive control"; https://web.archive.org/web/20180316101206/http://www.frisbee-project.eu/research/52-saving-energy-by-refrigeration-predictive-control.html; Available as early as Mar. 16, 2018; pp. 1-3.

Frisbee; "Frisbee european project—Superchilling! A new technology to have your food products fresher than fresh"; https://web.archive.org/web/20180316101206/http://www.frisbee-project.eu/research/50-superchilling.html; Available as early as Mar. 16, 2018; pp. 1-3.

Frisbee; "Frisbee european project—Taking Europe's temperature: Cold chain database"; http://www.frisbee-project.eu/news/89-taking-europe%E2%80°/099s-temperature-cold-chain-database.html; Mar. 18, 2013; pp. 1-2.

Frisbee; "Frisbee european project—Workpackages"; https://web.archive.org/web/20120210124516/http://www.frisbee-project.eu/workpackages.html; Available as early as Feb. 10, 2012; pp. 1-2.

Frisbee; "Simulate a cold chain"; https://frisbee-etool.irstea.fr; Available as early as 2020; pp. 1-3.

Gapud, Veny; "Food Safety Trends Exploring Implications of Mandatory Safety Standards in Retail and Foodservice"; https://www.foodsafetymagazine.com/magazine-archive1/december-2009january-2010/food-safety-trends-exploring-implications-of-mandatory-safety-standards-in-retail-and-foodservice/; Dec. 12, 2019; pp. 1-20.

Gaukler, Gary et al.; "Establishing Dynamic Expiration Dates for Perishables: An Application of RFID and Sensor Technology"; International Journal of Production Economics; vol. 193; Jul. 25, 2017; pp. 617-632.

GEIE/CEMA/ITP; "Deliverable D 8.3.1.3 Newsletter edited by GEIE for industrial use N°3"; http://www.frisbee-projecteu/images/result/FRISBEE_DEL_8.3.1.3.pdf; Mar. 13, 2012; pp. 1-10.

GEIE/CEMA/ITP; "Deliverable D8.3.1.2 Newsletter edited by GEIE for industrial use N°2"; http://www.frisbee-project.eu/images/result/FRISBEE_DEL_8.3.1.2.pdf; Oct. 27, 2011; pp. 1-10.

Giannakourou, M. C., et al.; "Application of a TTI-Based Distribution Management System for Quality Optimization of Frozen Vegetables at the Consumer End"; Journal of Food Science, vol. 68, Issue 1; Jan. 2003; pp. 201-209.

Hertog, M. L. A. T. M., et al.; "Shelf-life modelling for first-expired-first-out warehouse management"; Philosophical Transactions of the Royal Society; http://dx.doi.org/10.1098/rsta.2013.0306; 2014; pp. 1-15.

IBM; "DHL Breaks New Ground with RFID-Based Real-Time Tracking of Sensitive Shipments"; ftp://ftp.software.ibm.com/software/solutions/pdfs/ODC00298-USEN-00.pdf; Available as early as Mar. 2007; pp. 1-4.

IBM; "Focus on Food Safety"; https://www.ibm.com/downloads/cas/ZN9EWKRQ; Available at least as early as 2018; pp. 1-2.

INFRATAB; "Infratab Freshtime RF Sensor Blockchain Solutions for the Fresh Seafood Cold Chain"; https://web.aimglobal.org/external/wcpages/wcecommerce/eComItemDetailsPage.aspx?ItemID=656; 2019; pp. 1-5.

Jedermann, Reiner, et al.; "Communication techniques and challenges for wireless food quality monitoring"; Philosophical Transactions of the Royal Society; http://dx.doi.org/10.1098/rsta.2013.0304; 2014; pp. 1-18.

Jedermann, Reiner, et al.; "Reducing food losses by intelligent food logistics"; Philosophical Transactions of the Royal Society; http://dx.doi.org/10.1098/rsta.2013.0302; 2014; pp. 1-20.

Kader, A. A.; "Pre- and Postharvest Factors Affecting Fresh Produce Quality, Nutritional Value, and Implications for Human Health"; Proceedings of the International Congress of Food Production and the Quality of Life, Sassari (Italy) Sep. 4-8, 2000, vol. 1, pp. 109-119.

Ketzenberg, M., et al.; "Expiration Dates and Order Quantities for Perishables"; European Journal of Operational Research; vol. 266, Issue 2; Apr. 2018; pp. 569-584.

Ketzenberg, M., et al.; "Managing Perishables with Time and Temperature History"; Production and Operations Management; vol. 24, Issue 1; Jan. 2015; pp. 54-70.

Ketzenberg, M., et al.; "The Value of RFID Technology Enabled Information to Manage Perishables"; https://pdfs.semanticscholar.org/bded/16af2e689b4fdcea7f8421f6e012a6041324.pdf; Apr. 2009; pp. 1-37.

Koutsoumanis, K., et al.; "Development of a safety monitoring and assurance system for chilled food product"; International Journal of Food Microbiology, vol. 100; 2005; pp. 253-260.

Leake, Linda L.; "The Search for Shelf Life Solutions"; https://www.ift.org/news-and-publications/food-technology-magazine/issues/2007/n ovember/columns/laboratory?p.=viewall; Nov. 1, 2007; pp. 1-8.

McBeath, Bill; "Winning the Freshness Wars: Creating Shopper Loyalty and Improving Profitability in Retail Grocery"; https://www.zestlabs.com/wp-content/uploads/2016/11/ZL_WP_FreshnessWars_060415.p.df; Available as early as Feb. 2013; pp. 1-16.

Mehring, Peter; "Blockchain for Food Safety—Addressing the Challenges"; https://www.zestlabs.com/will-blockchain-solve-food-safety-challenges/; Sep. 26, 2018; pp. 1-4.

Mehring, Peter; "Zest Labs Ceo Peter Mehring on the Walmart Lawsuit"; https://www.zestlabs.com/zest-labs-ceo-peter-mehring-walmart-lawsuit/; Aug. 1, 2018; pp. 1-4.

Mitrokotsa et al.; "Integrated Rfid and Sensor Networks: Architectures and Applications"; https://pdfs.semanticscholar.org/e5b0/c2a44971 bad209cbf66afb6c825f89792723.pdf; Jun. 22, 2009; pp. 511-536.

NBC Bay Area; "Tech Company Helps Inspect Food During Shutdown"; https://www.nbcbayarea.com/news/tech/tech-company-helps-inspect-food-during-shut down_bay-area/4851; Jan. 11, 2019; pp. 1-6.

NRDC; "Wasted: How America is Losing up to 40 Percent of Its Food From Farm to Fork Landfill"; https://www.nrdc.org/sites/default/files/wasted-2017-report.pdf; Available as early as Aug. 2017; pp. 1-58.

Opatova, H.; "Deliverable 8.2.2.1 Organisation of a Workshop in Prague 2011 at International Congress of Refrigeration"; http://www.frisbee-project.eu/images/result/FRISBEE_DEL_8.2.2.1.pdf; Oct. 27, 2011; pp. 1-8.

Payne, Kevin; " New Verizon Ad Sheds Light on Important Food Safety Issues"; https://www.zestlabs.com/new-verizon-ad-sheds-light-on-important-food-safety-iss ues/; Dec. 15, 2017; pp. 1-4.

Payne, Kevin; "Agriculture Technology and "The Messy Middle""; https://www.zestlabs.com/agriculture-technology-messy-middle/; Jun. 25, 2019; pp. 1-4.

Payne, Kevin; "Are You Ready to Make 2018 Your Best Year Ever?" https://www.zestlabs.com/are-you-ready-to-make-2018-your-best-year-eved; Feb. 13, 2018; pp. 1-4.

Payne, Kevin; "Blockchain for Fresh Food Supply Chains—Reality Sets in?"; https://www.zestlabs.com/blockchain-fresh-supply-chains-reality/; May 7, 2019; pp. 1-4.

Payne, Kevin; "Cold Chain Visibility: Who's Winning the Freshness Wars?"; https://www.zestlabs.com/cold-chain-visibility-freshness-wars/; Apr. 9, 2019; pp. 1-4.

Payne, Kevin; "Cold Supply Chain Variability—the Impact of Delays"; https://www.zestlabs.com/cold-supply-chain-variability/; Apr. 23, 2019; pp. 1-4.

Payne, Kevin; "Earth Day 2019 and Looking Ahead to 2020"; https://www.zestlabs.com/earth-day-2019/; Apr. 30, 2019; pp. 1-4.

Payne, Kevin; "Finding the Right Tools: Can Blockchain and IOT Fix the Fresh Food Supply Chain? —Register for the Webinar";

(56) References Cited

OTHER PUBLICATIONS https://www.zestlabs.com/finding-the-right-tools-can-blockchain-and-iot-fix-the- fresh-food-supply-chain-register-for-the-webinari; Feb. 27, 2018; pp. 1-4.
Payne, Kevin; "Food Grower and Supplier Challenges: The Top 10"; https://www.zestlabs.com/food-growers-suppliers-challenges/; Feb. 19, 2019; pp. 1-4.
Payne, Kevin; "Food Labels and Food Waste—A Solution"; https://www.zestlabs.com/food-labels-food-waste/; Mar. 12, 2019; pp. 1-4.
Payne, Kevin; "Food Safety Tips: Three Things to Consider"; https://www.zestlabs.com/food-safety-tips-three-things-to-consider/; Jul. 2, 2019; pp. 1-4.
Payne, Kevin; "Fresh Produce and Health: What's the Connection?"; https://www.zestlabs.com/fresh-produce-health-interrelationship/; Apr. 2, 2019; pp. 1-4.
Payne, Kevin; "Grocery Shopper Trends 2019: Key Insights"; https://www.zestlabs.com/grocery-shopper-trends-2019-key-insights/; Jul. 23, 2019; pp. 1-4.
Payne, Kevin; "How to Feed a Hungry Planet: Food for Thought"; https://www.zestlabs.com/feed-a-hungry-planet/; Aug. 6, 2019; pp. 1-4.
Payne, Kevin; "Hyped Up? Blockchain and Why a Hybrid Model is Best"; https://www.zestlabs.com/hyped-up-blockchain-the-fresh-food-supply-chain-and-why -a-hybrid-model-is-best/; Jan. 30, 2018; pp. 1-4.
Payne, Kevin; "I'll Never Look at Strawberries the Same Way"; https://www.zestlabs.com/ill-never-look-at-strawberries-the-same-way/; Dec. 15, 2017; pp. 1-4.
Payne, Kevin; "Improving Operational Efficiency: TQM for the Fresh Food Supply Chain"; https://www.zestlabs.com/improving-operational-efficiency-deming-drucker/; Aug. 27, 2019; pp. 1-4.
Payne, Kevin; "Increasing Trucking Costs Further Squeezes Grocery Margins—Don't Waste Your Money!" https://www.zestlabs.com/increasing-trucking-costs-further-squeezes-grocery-marg ins-dont-waste-your-money/; Feb. 6, 2018; pp. 1-4.
Payne, Kevin; "IoT Sensors and Reducing Food Waste"; https://www.zestlabs.com/iot-sensors-reduce-food-waste/; Feb. 12, 2019; pp. 1-4.
Payne, Kevin; "Millennials Want True Transperency"; https://www.zestlabs.com/millennials-want-true-transparency/; Jan. 9, 2018; pp. 1-4.
Payne, Kevin; "Myth Busting: Produce Shrink is Caused at the Store"; https://www.zestlabs.com/myth-busting-produce-shrink-occurs-at-the-store/; Feb. 20, 2018; pp. 1-4.
Payne, Kevin; "New Zest Fresh for Produce Modules: Rapid Implementations and Faster ROI"; https://www.zestlabs.com/zest-fresh-produce-modules/; Jul. 10, 2019; pp. 1-4.
Payne, Kevin; "Online Grocery Shopping Options Abound But . . ."; https://www.zestlabs.com/online-grocery-shopping/; Feb. 5, 2019; pp. 1-4.
Payne, Kevin; "Preventing Food Waste: Multiple Approaches"; https://www.zestlabs.com/preventing-food-waste-multiple-approaches/; Jul. 16, 2019; pp. 1-4.
Payne, Kevin; "Proactive Food Safety: Moving the Industry Forward"; https://www.zestlabs.com/proactive-food-safety/; Aug. 13, 2019; pp. 1-4.
Payne, Kevin; "Produce Marketing: Brandstorm Offers a Wealth of Insights"; https://www.zestlabs.com/produce-marketing-ideas; Feb. 26, 2019; pp. 1-4.
Payne, Kevin; "Reducing Fresh Food Waste: Addressing the Problem"; https://www.zestlabs.com/reducing-fresh-food-waste-problem/; Mar. 5, 2019; pp. 1-4.
Payne, Kevin; "Rethinking Food Safety and the Supply Chain"; https://www.zestlabs.com/rethinking-food-safety-supply-chain/; May 14, 2019; pp. 1-5.
Payne, Kevin; "Salad Kits: How to Ensure Freshness"; https://www.zestlabs.com/salad-kits-fresh/; Apr. 16, 2019; pp. 1-4.
Payne, Kevin; "Shelf-life Variability at Grocery Stores: Half-bad is Not Good"; https://www.zestlabs.com/shelf-life-variability-among-leading-grocery-stores/; Jun. 10, 2019; pp. 1-4.
Payne, Kevin; "Start the Year Fresh!" https://www.zestlabs.com/start-the-year-fresh/; Jan. 16, 2018; pp. 1-4.
Payne, Kevin; "Supply Chain Waste: Can We Fix the Problem? (Yes)"; https://www.zestlabs.com/supply-chain-waste/; Jul. 30, 2019; pp. 1-5.
Payne, Kevin; "Sustainability and the Supply Chain"; https://www.zestlabs.com/sustainability-supply-chain/; Jun. 18, 2019; pp. 1-4.
Payne, Kevin; "Sustainability or Greenwashing" https://www.zestlabs.com/sustainability-or-greenwashing/; Jan. 23, 2018; pp. 1-4.
Payne, Kevin; "The 'Best If Used by' Date Label: Will It Reduce Food Waste?"; https://www.zestlabs.com/best-if-used-by-date-label/; Jun. 4, 2019; pp. 1-4.
Payne, Kevin; "The Emergence of Brand Marketing in Produce"; https://www.zestlabs.com/brand-marketing-produce/; Aug. 20, 2019; pp. 1-4.
Payne, Kevin; "The Grocery Shopping Experience: Fresh Foods, Fresh Ideas"; https://www.zestlabs.com/grocery-shopping-experience-fresh-foods/; May 21, 2019; pp. 1-4.
Payne, Kevin; "To Use or Not to Use—What's Up With Date Labels" https://www.zestlabs.com/date-label/; Jan. 2, 2018; pp. 1-4.
Payne, Kevin; "Want to Improve Your Grocery Margins? Take a Look at Your Supply Chain"; https://www.zestlabs.com/want-to-improve-your-grocery-margins-take-a-look-at-you r-supply-chain/; Dec. 19, 2017; pp. 1-4.
Payne, Kevin; "World Hunger Day 2019: Sustainability"; https://www.zestlabs.com/world-hunger-day-2019-sustainability/; May 28, 2019; pp. 1-4.
Payne, Kevin; "Your Technology Roadmap for Digital Transformation"; https://www.zestlabs.com/technology-roadmap/; Mar. 26, 2019; pp. 1-4.
Payne, Kevin; "A Picture Is Worth . . ."; https:!/www.zestlabs.com/a-picture-is-worth/; Apr. 3, 2018; pp. 1-4.
Payne, Kevin; "Before and After—The Benefits of Digital Transformation"; https://www.zestlabs.com/benefits-digital-transformation/; Jan. 29, 2019; pp. 1-5.
Payne, Kevin; "Being Proactive: What We Can Learn from Football"; https://www.zestlabs.com/being-proactive-learn-from-football/; Jul. 17, 2018; pp. 1-4.
Payne, Kevin; "Digital Transformation Technology: Is It Finally Time?"; https://www.zestlabs.com/digital-transformation-technology/; Aug. 7, 2018; pp. 1-4.
Payne, Kevin; "Experience the Many Benefits of Family Meals"; https://www.zestlabs.com/benefits-family-meals/; Sep. 3, 2019; pp. 1-4.
Payne, Kevin; "First Principles Thinking and the Fresh Food Supply Chain"; https://www.zestlabs.com/first-principles-thinking/; Oct. 2, 2018; pp. 1-4.
Payne, Kevin; "Five Days? The Causes of Shelf-life Variability"; https://www.zestlabs.com/five-days-shelf-life-variability!; Nov. 20, 2018; pp. 1-4.
Payne, Kevin; "Food Service Delivery: This Isn't What I Ordered!"; https://www.zestlabs.com/isnt-what-ordered/; Aug. 28, 2018; pp. 1-4.
Payne, Kevin; "Food Spoilage: The Impact on Your Business"; https://www.zestlabs.com/food-spoilage-impact-business/; Jan. 15, 2019; pp. 1-4.
Payne, Kevin; "Food Sustainability Goals: Noble But Are They Viable?"; https://www.zestlabs.com/food-sustainability-goals/; Aug. 14, 2018; pp. 1-4.
Payne, Kevin; "Fresh Food Industry Trends 2019—Our Predictions"; https://www.zestlabs.com/fresh-food-industry-trends-2019/; Jan. 2, 2019; pp. 1-4.
Payne, Kevin; "Fresh Food Industry Trends from 2018"; https://www.zestlabs.com/fresh-food-industry-trends-2018/; Dec. 11, 2018; pp. 1-4.
Payne, Kevin; "Fresh Food Sustainability—It's More Than Field to Fork"; https://www.zestlabs.com/fresh-food-sustainability/; Jan. 22, 2019; pp. 1-4.
Payne, Kevin; "Freshness Capacity: Strawberries Are Like Your Cell Phone . . ."; https://www.zestlabs.com/your-fresh-strawberries-are-like-your-cellphone/; Jul. 10, 2018; pp. 1-4.

(56) References Cited

OTHER PUBLICATIONS

Payne, Kevin; "Grocers Are Applying Artificial Intelligence"; https://www.zestlabs.com/grocers-turning-adificial-intelligence/; Oct. 9, 2018; pp. 1-4.
Payne, Kevin; "Growers and Suppliers—What Really Happens in the Food Supply Chain"; https://www.zestlabs.com/what-happens-fresh-food-supply-chain/; Apr. 24, 2018; pp. 1-5.
Payne, Kevin; "Improving Post-Harvest Operational Efficiency"; https://www.zestlabs.com/improving-operational-efficiency/; Sep. 18, 2018; pp. 1-4.
Payne, Kevin; "Is Your Fresh Food Supply Chain Stuck in The '60s?"; https://www.zestlabs.com/is-your-fresh-food-supply-chain-stuck-in-the-60s/; Mar. 13, 2018; pp. 1-4.
Payne, Kevin; "It's (Past) Time for Freshness Management"; https://www.zestlabs.com/managing-fresh-food-shelf-life/; Nov. 27, 2018; pp. 1-4.
Payne, Kevin; "It's Like Waze for the Fresh Food Supply Chain"; https://www.zestlabs.com/waze-fresh-food-supply-chain/; Apr. 10, 2018; pp. 1-5.
Payne, Kevin; "Let's Celebrate National Salad Month!"; https://www.zestlabs.com/lets-celebrate-national-salad-month/; May 1, 2018; pp. 1-4.
Payne, Kevin; "Let's Start At the Beginning"; https://www.zestlabs.com/lets-start-at-the-beginning/; May 15, 2018; pp. 1-4.
Payne, Kevin; "Margins Matter—Don't Get Squeezed"; https://www.zestlabs.com/6931-2/; Apr. 17, 2018; pp. 1-4.
Payne, Kevin; "Perishable Food Waste Cuts Profits & Raises Greenhouse Gases"; https://www.zestlabs.com/food-waste-profits-greenhouse-gases/; Sep. 11, 2018; pp. 1-4.
Payne, Kevin; "PMA Fresh Summit 2018—Wow!"; https://www.zestlabs.com/pma-fresh-summit/; Oct. 23, 2018; pp. 1-4.
Payne, Kevin; "Pma's Fresh Summit: Eat Up!"; https://www.zestlabs.com/pma-fresh-summit-2018/; Oct. 16, 2018; pp. 1-4.
Payne, Kevin; "Poor Quality Produce: Never Going Back Again"; https://www.zestlabs.com/never-going-back-again/; Jul. 3, 2018; pp. 1-4.
Payne, Kevin; "Premature Food Spoilage: Uh Oh, It's the Fuzz!"; https://www.zestlabs.com/uh-oh-its-the-fuzz/; Jun. 19, 2018; pp. 1-4.
Payne, Kevin; "Produce Shelf Life Extenders and Fresh Food Waste"; https://www.zestlabs.com/shelf-life-extenders-food-waste!; Nov. 13, 2018; pp. 1-4.
Payne, Kevin; "Refed: Committed to Reducing U.S. Food Waste"; https://www.zestlabs.com/refed-committed-reducing-waste/; Oct. 30, 2018; pp. 1-4.
Payne, Kevin; "Romaine Lettuce Labeling—Zest Fresh Can Help"; https://www.zestlabs.com/romaine-lettuce-labeling/; Dec. 4, 2018; pp. 1-4.
Payne, Kevin; "Saving Money Day 1—Invest $1, Get $9 Back"; https://www.zestlabs.com/saving-money-day-1/; Nov. 6, 2018; pp. 1-4.
Payne, Kevin; "September Is National Family Meals Month"; https://www.zestlabs.com/september-family-meals-month/; Sep. 4, 2018; pp. 1-4.
Payne, Kevin; "Shelf-life Variability in Produce: The Five Causes"; https://www.zestlabs.com/shelf-life-variability-produce-five-causes/; Jan. 8, 2019; pp. 1-4.
Payne, Kevin; "Solving the Problem of Fresh Produce Waste"; https://www.zestlabs.com/solving-problem-fresh-food-waste/; Dec. 18, 2018; pp. 1-4.
Payne, Kevin; "Stay Cool! (and Visit Us at United Fresh!)"; https://www.zestlabs.com/stay-cool-and-visit-us-at-united-fresh/; Jun. 5, 2018; pp. 1-4.
Payne, Kevin; "Stop Doing That!"; https://www.zestlabs.com/stop-doing-that/; May 29, 2018; pp. 1-4.
Payne, Kevin; "Supply Chain Performance:The Fox and the Henhouse"; https://www.zestlabs.com/fox-hen-house!; Jun. 26, 2018; pp. 1-4.

Payne, Kevin; "The Fresh Food Industry and Charles Darwin"; https://www.zestlabs.com/charles-darwin-fresh-food-industry/; Aug. 21, 2018; pp. 1-4.
Payne, Kevin; "The Game of (Shelf) Life"; https://www.zestlabs.com/game-shelf-life/; Sep. 25, 2018; pp. 1-4.
Payne, Kevin; "Timing Is Everything—The Impact of Cut-To-Cool Time on Freshness"; https://www.zestlabs.com/timing-is-everything-the-impact-of-cut-to-cool-time-on- freshness/; May 8, 2018; pp. 1-5.
Payne, Kevin; "What to do to Build Grocery Store Loyalty?"; https://www.zestlabs.com/grocery-store-loyalty/; Jul. 24, 2018; pp. 1-4.
Payne, Kevin; "What? No Bacon? (Cue Ominous Music)"; https://www.zestlabs.com/what-no-bacon-cue-ominous-music/; Mar. 6, 2018; pp. 1-5.
Payne, Kevin; "What's in the Bag?"; https://www.zestlabs.com/whats-in-the-bag/; May 22, 2018; pp. 1-4.
Payne, Kevin; "Where's the Beef (Been)?"; https://www.zestlabs.com/wheres-the-beef-been/; Mar. 27, 2018; pp. 1-5.
Payne, Kevin; "Zest Labs Offers Fresh Wishes for the New Year"; https://www.zestlabs.com/zest-labs-fresh-wishes-new-year/; Dec. 24, 2018; pp. 1-4.
ReFED; "A Roadmap to Reduce U.S. Food Waste by 20 Percent"; https://www.refed.com/downloads/ReFED_Report_2016.pdf; 2016; pp. 1-96.
ReFED; "Restaurant Food Waste Action Guide"; https://www.refed.com/downloads/Restaurant_Guide_Web.pdf; 2018; pp. 1-44.
ReFED; "Retail Food Waste Action Guide"; https://www.refed.com/downloads/Retail_Guide_Web.pdf; 2018; pp. 1-44.
Ruiz-Garcia, Luis et al.; "Monitoring Cold Chain Logistics by Means of RFID"; http://cdn.intechweb.org/pdfs/8493.pdf; Feb. 1, 2010; pp. 1-16.
Ryan, John; "Why Blockchain Will Be Used to Improve Distribution Food Safety, Quality, and Traceability"; https://www.foodsafetymagazine.com/enewsletter/why-blockchain-will-be-used-to-im prove-distribution-food-safety-quality-and-traceability/; Feb. 5, 2019; pp. 1-3.
Scalco, Dan; "5 Ways to Ensure Meals Stay Fresh and Safe in Transit"; https://www.zestlabs.com/meals-stay-fresh-safe-transit/; Jun. 12, 2018; pp. 1-4.
Scotto Di Tella, F.; "Deliverable D8.3.1.1 Newsletter edited by Geie for industrial use N°1"; http://www.frisbee-project.eu/images/result/FRISBEE_DEL_8.3.1.1.pdf; May 6, 2011; pp. 1-9.
Shacklett, Mary; "Customer Retention and Growth in Today's Competitive Retail Grocery Environment"; https://www.zestlabs.com/downloads/Food-Freshness-and-Customer-Satisfaction-Transworld-Research-Apr.-2019.pdf; Apr. 2019; pp. 1-7.
Shacklett, Mary; "Improving Profits and Operational Efficiency on the Farm"; https://www.zestlabs.com/downloads/Improving-Operational-Efficiency-on-the-Farm- Transworld-Research-2018.pdf; Available as early as 2018; pp. 1-6.
Shacklett, Mary; "Optimizing Profit Margins in a Changing Retail Grocery Industry"; https://www.zestlabs.com/downloads/Optimizing-Profit-Margins-Transworld.pdf; 2018; pp. 1-10.
Siawsolit, Chokdee et al.; "The Value of Demand Information in Omni-Channel Grocery Retailing"; https://www.researchgate.net/publication/331048136_The_Value_of_Demand_Information_in_Omni-Channel_Grocery_Retailing; Available as early as Jan. 2019; pp. 1-11.
Stahl, Valerie et al.; "Deliverable D.3.2.4.2 Literature review and experimental data of chilled and frozen meat quality and safety models"; http://www.frisbee-project.eu/images/result/ FRISBEE_DEL_3.2.4.2.pdf; Jun. 6, 2011; pp. 1-28.
Sunny George, Gwanpua; "Deliverable D3.2.4.1 Literature review and experimental data of chilled apple quality models"; http://www.frisbee-project.eu/images/result/FRISBEE_DEL_3.2.4.1.pdf; Mar. 1, 2011; pp. 1-24.
Swedberg, Claire; "DOD Considers RFID-based Solutions for Tracking Food's Shelf Life"; https://www.rfidjournal.com/articles/pdf?11423; Feb. 11, 2014; pp. 1-3.
Swedberg, Claire; "Researchers Seek to Reduce Wastage for First-Strike Rations"; https://www.rfidjournal.com/articles/pdf?9162; Jan. 26, 2012; pp. 1-4.

(56) References Cited

OTHER PUBLICATIONS

Swedberg, Claire; "Schuitema Ponders Future of Fresh-Chain Pilot"; https://www.rfidjournal.com/articles/pdf?3793; Dec. 10, 2007; pp. 1-4.
Swedberg, Claire; "Starbucks Keeps Fresh with RFID"; https://www.rfidjournal.com/articles/view?2890; Dec. 13, 2006; pp. 1-1.
Taoukis, P. S., et al.; "Applicability of Time-Temperature Indicators as Shelf Life Monitors of Food Products"; Journal of Food Science; vol. 54, Issue 4; Jul. 1989; pp. 783-788.
Taoukis, P. S., et al.; "Use of time-temperature integrators and predictive modelling for shelf life control of chilled fish under dynamic storage conditions"; International Journal of Food Microbiology, vol. 53; 1999; pp. 21-31.
Taoukis, Petros et al.; "Deliverable D.2.1.2 Temperature monitoring techniques and traceability systems along the cold chain";http://www.frisbee-project.eu/images/result/ FRISBEE_DEL_2%201% 202.pdf; Jul. 26, 2011; pp. 1-28.
Taoukis, Petros; "Deliverable D 3.2.4.4 Literature review and experimental data of frozen milk products and vegetables quality models"; http://www.frisbee-project.eu/images/result/ FRISBEE_DEL_3-2-4-4.pdf; Jun. 6, 2011; pp. 1-24.
This New World by Huffpost; "Eating Ugly: The Food Waste That Could Refeed America"; https://www.facebook.com/ThisNewWorldHuffPost/videos/428476821288487; Apr. 22, 2019; pp. 1-9.
Trust in Foodtm; "Sustainability Research Report 2019"; https://www.zestlabs.com/downloads/Trust-In-Food-Sustainability-Survey-2019.pdf; Available as early as Jul. 18, 2019; pp. 1-19.
United States Army Medical Command; "U.S. Army Veterinary Command Guidelines and Procedures"; https://www.dla.mil/Portals/104/Documents/TroopSupport/Subsistence/Rations/qapub s/medcom/ 40-13.pdf; Feb. 13, 2006; pp. 1-171.
Wells, John H., et al.; "A Kinetic Approach to Food Quality Prediction using Full-History Time-Temperature Indicators"; Journal of Food Science; vol. 53, Issue 6; Nov. 1988; pp. 1866-1871.
Wells, John H., et al.; "A Quality-Based Inventory Issue Policy for Perishable Foods"; Journal of Food Processing & Preservation; vol. 12, Issue 4; Jan. 1989; pp. 271-292.
Wells, John Henry, et al.; "Application of Time-Temperature Indicators in Monitoring Changes in Quality Attributes of Perishable and Semiperishable Foods"; Journal of Food Science; vol. 53, Issue 1; Jan. 1988; pp. 148-152, 156.
Weston, L.A. et. al.; "Preharvest Factors Affecting Postharvest Quality of Vegetables"; HortScience; vol. 32(5), Aug. 1997, pp. 812-816.
Williamson, Katie et al.; "Climate Change Needs Behavior Change"; https://www.zestlabs.com/downloads/2018-Ccnbc-Report.pdf; 2018; pp. 1-22.
Zelem, MC.; "Deliverable D.2.3.1 National legal and ethical requirements for the surveys"; http://www.frisbee-project.eu/images/result/ FRISBEE_DEL_2.3.1.pdf; Jun. 23, 2011; pp. 1-68.
*Zest Labs, Inc.* v *Walmart*; Bohling, Joshua; "Transcript of the Testimony of Bohling, Joshua"; Bushman Court Reporting; Case No. 4:18-CV-00500-JM; Aug. 15-16, 2019; pp. 5-6, 47-48, 52-69, 78, 80-82, 85, 87, 98-102, 107-134, 137-145, 158-163, 182-184, 209-210, 233-234, 239-242, 246, and 357.
*Zest Labs, Inc.* v *Walmart*; Dickinson, Q. Todd; "Expert Report of Q. Todd Dickinson"; United States District Court for the Eastern District of Arkansas; Case No. 4:18-CV-00500-JM; Oct. 29, 2019; pp. 1-33.
*Zest Labs, Inc.* v *Walmart*; Kunin, Stephen G.; "Rebuttal Expert Report of Stephen G. Kunin"; United States District Court for the Eastern District of Arkansas; Case No. 4:18-CV-00500-JM; Nov. 25 2019; pp. 1-38.
*Zest Labs, Inc.* v *Walmart*; Zest Labs, Inc. et al.; "Complaint"; United States District Court for the Eastern District of Arkansas; Case No. 4:18-CV-00500-JM; Aug. 1, 2018; pp. 1-26.
Zest Labs; "Blockchain for Supply Chains"; https://www.zestlabs.com/challenges/blockchain-for-supply-chains/; Available as early as Jul. 18, 2019; pp. 1-4.
Zest Labs; "Food Safety and the Supply Chain"; https://www.zestlabs.com/challenges/food-safety/; Available as early as Jul. 18, 2019; pp. 1-5.
Zest Labs; "Food Supplier Operational Efficiency"; https://www.zestlabs.com/challenges/food-supplier-operational-efficiency/; Available as early as Jul. 18, 2019; pp. 1-5.
Zest Labs; "Food Waste is a Significant Problem"; https://www.zestlabs.com/challenges/food-waste-challenge/; Available as early as Jul. 18, 2019; pp. 1-6.
Zest Labs; "Fresh Food Supply Chain"; https://www.zestlabs.com/challenges/fresh-food-supply-chain/; Available as early as Jul. 18, 2019; pp. 1-5.
Zest Labs; "Fresh Food Sustainability"; https://www.zestlabs.com/challenges/fresh-food-sustainability/; Available as early as Jul. 18, 2019; pp. 1-4.
Zest Labs; "Fresh Produce"; http://www.zestlabs.com/fresh-produce; Available as early as Oct. 21, 2017; pp. 1-14.
Zest Labs; "On-Demand Delivery"; https://www.zestlabs.com/on-demand-delivery/; Available as early as Oct. 22, 2017; pp. 1-7.
Zest Labs; "On-demand meal quality visibility from the restaurant to consumer delivery"; https://www.zestlabs.com/zest-delivery/; Available as early as Oct. 22, 2017; pp. 1-7.
Zest Labs; "Post-Harvest Technology"; https://www.zestlabs.com/challenges/post-harvest-technology/; Available as early as Jul. 18, 2019; pp. 1-8.
Zest Labs; "The Freshest Produce"; https://www.zestlabs.com/resources; Available as early as May 2, 2018; pp. 1-16.
Zest Labs; "Zest Fresh - Deep Dive"; https://www.zestlabs.com/resources; Available as early as May 2, 2018, pp. 1-15.
Zest Labs; "Zest Fresh Differentiation"; https://www.zestlabs.com/zest-fresh-differentiation/; Available as early as Jul. 18, 2019; pp. 1-6.
Zest Labs; "Zest Fresh for Beef, Poultry, Pork and Seafood"; https://www.zestlabs.com/zest-fresh-for-protein/; Available as early as Jul. 18, 2019; pp. 1-5.
Zest Labs; "Zest Fresh for Grocers"; https://www.zestlabs.com/zest-fresh-for-produce-for-grocers/; Available as early as Jul. 18, 2019; pp. 1-13.
Zest Labs; "Zest Fresh for Growers, Packers, and Shippers"; https://www.zestlabs.com/zest-fresh-for-growers-and-suppliers/; Available as early as Jul. 18, 2019; pp. 1-17.
Zest Labs; "Zest Fresh for Restaurants"; https://www.zestlabs.com/zest-fresh-for-produce-for-restaurants/; Available as early as Jul. 18, 2019; pp. 1-13.
Zest Labs; "Zest Fresh Grower Testimonial"; https://www.zestlabs.com/resources; Available as early as May 2, 2018; pp. 1-13.
Zest Labs; "Zest Fresh Overview"; https://www.zestlabs.com/resources; Available as early as May 2, 2018; pp. 1-19.
Zest Labs; "Zest Fresh Use Cases"; https://www.zestlabs.com/zest-fresh-use-cases/; Available as early as Jul. 18. 2019; pp. 1-6.
Zest Labs; "Zest Fresh: Pallet-level Quality Management from Harvest to Store"; http://www.zestlabs.com/zest-fresh; Available as early as Oct. 29, 2017; pp. 1-10.
Zest Labs; "Zest Labs Overview"; https://www.zestlabs.com/resources; Available as early as Aug. 1, 2018; pp. 1-13.
Zest Labs; ". . . Not Worth a Thousand Words—Why Traditional Temperature Loggers and Imaging Technologies are Inadequate to Determine Freshness and Reduce Waste"; https:// www.zestlabs.com/wp-content/uploads/2018/03/WP-05-0318-Not-Worth-A-Thous and-Words.pdf; Mar. 5, 2018; pp. 1-6.
Zest Labs; "10 Limitations of Traditional Temperature Data Loggers and Why They're No Longer Adequate for the Cold Chain"; https://www.zestlabs.com/wp-content/uploads/2018/05/PB-04-0418-10-Limitations-of -Data-Loggers.pdf; May 4, 2018; pp. 1-3.
Zest Labs; "Before and After—the Benefits of Digital Transformation in the Fresh Food Supply Chain"; https://www.zestlabs.com/downloads/Before-and-After-Digital-Transformation.pdf; Jan. 13, 2019; pp. 1-6.
Zest Labs; "Blockchain and Achieving True Transparency—Proactively Managing Food Safety and Freshness with Blockchain and IoT Technologies"; https://www.zestlabs.com/wp-content/ uploads/ 2018/01/WP-08-0118.Blockchain.and_.Achieving.True_.Transparency-1.pdf; Jan. 8, 2018; pp. 1-4.

(56) References Cited

OTHER PUBLICATIONS

Zest Labs; "Blockchain and Its Value to Suppliers"; https://www.zestlabs.com/downloads/Blockchain-and-Its-Value-to-Suppliers.pdf; Available as early as Jul. 18, 2019; pp. 1-5.

Zest Labs; "Comparing Pallet—and Trailer-level Temperature Monitoring—Implications on Quality, Freshness, Traceability and Profitability for Retail Grocers"; https://www.zestlabs.com/wp-content/uploads/2018/03/WP-04-0318-Pallet-vs-Trailer .pdf; Mar. 4, 2018; pp. 1-4.

Zest Labs; "Freshness Baseline Study—Sample Report"; http://www.zestlabs.com/wp-content/uploads/2018/03/Zest-Labs-Sample-Baseline-Rep ort.pdf; Available as early as Mar. 2018; pp. 1-11.

Zest Labs; "Freshness Myths—False Beliefs That Lead to Food Waste"; https://www.zestlabs.com/downloads/Freshness-Myths.pdf; Aug. 7, 2018; pp. 1-5.

Zest Labs; "Half-bad Is Not Good"; https://www.zestlabs.com/downloads/Grocery-Store-Variability.pdf; Jun. 15, 2019; pp. 1-11.

Zest Labs; "Improve Operational Efficiency—Optimize Labor and Process Adherence to Reduce Costs"; https://www.zestlabs.com/downloads/Improving-Operational-Efficiency.pdf; Available as early as Jul. 18, 2019; pp. 1-3.

Zest Labs; "Improving Quality and Profitability for Retail Grocers—The Benefits of Pallet-level Monitoring for the Fresh and Perishable Food Cold Chain"; https://www.zestlabs.com/wp-content/uploads/2017/12/WP-01-1117.Improving.Quality .and_.Profitability.for_.Retail.Grocers.pdf; Nov. 1, 2017; pp. 1-8.

Zest Labs; "Let's Start at the Beginning—Reducing Shrink Begins at Harvest"; https://www.zestlabs.com/wp-content/uploads/2018/05/WP-12-0518-Lets-Start-at-the -Beginning.pdf; May 12, 2018; pp. 1-4.

Zest Labs; "Margins Matter—Reducing Fresh Food Waste to Improve Product Margins by 6% or More"; https://www.zestlabs.com/wp-content/uploads/2018/04/WP-11-0418-Margins-Matter-1. pdf; Apr. 11, 2018; pp. 1-6.

Zest Labs; "Measuring and Managing Operational Efficiency for Growers and Suppliers"; https://www.zestlabs.com/downloads/Zest-Fresh-Metrics-Datasheet.pdf; Aug. 25, 2019; pp. 1-5.

Zest Labs; "Monitoring the Safety and Quality of Fresh, Frozen and Processed Foods"; https://www.zestlabs.com/wp-content/uploads/2016/03/IN-SB-Fresh Prod uce_Restau ran tFoodService_031016.pdf; Mar. 10, 2016; pp. 1-2.

Zest Labs; "Pallet-level Quality Management from Harvest to Store"; https://www.zestlabs.com/wp-content/uploads/2016/03/IN_SB_FoodIndustry_ProduceGr owers_031016.pdf; Mar. 10, 2016; pp. 1-2.

Zest Labs; "Poor Customer Experiences—Half-Bad is Not Good! A Shelf-Life Variability Study"; https://www.zestlabs.com/downloads/Variability-Infographic.pdf; Available as early as Jul. 2019; pp. 1-1.

Zest Labs; "Proactive Freshness Management: Modernizing the Fresh Food Supply Chain to Reduce Waste and Improve Profitability"; https://www.zestlabs.com/downloads/Proactive-Freshness-Management.pdf; Feb. 6, 2019; pp. 1-7.

Zest Labs; "Reduce Shrink, Improve Profitability and Quality for Fresh Food"; https://www.zestlabs.com/wp-content/uploads/2016/03/IN-SB-Fresh Produce_RetailG ro cers_031016.pdf; Mar. 10, 2016; pp. 1-3.

Zest Labs; "Shelf-life Variability Begins in the Field—Produce Pallets Harvested on the Same Day Vary by as Much as 86 Percent, Contributing to Shrink and Lost Profits"; https://www.zestlabs.com/wp-content/uploads/2018/02/WP-100218-Shelf-life-Variab ility.pdf; Feb. 10, 2018; pp. 1-4.

Zest Labs; "Strawberries—Shelf-Life Variability"; https://www.zestlabs.com/downloads/Zest-Fresh-Strawberries-Report.pdf; Available as early as Jul. 2019; pp. 1-2.

Zest Labs; "The Best of Zest 2018—A Collection of Our Most Popular Blogs"; https://www.zestlabs.com/downloads/The-Best-of-Zest-2018.pdf; Available as early as 2018; pp. 1-15.

Zest Labs; "The ZIPR Code Freshness Metric—Dynamically providing the current freshness of each pallet to help you intelligently manage product and reduce shrink throughout the fresh food supply chain"; https://www.zestlabs.com/downloads/The-ZIPR-Code.pdf; Jun. 1, 2018; pp. 1-3.

Zest Labs; "Today, You Saved $67,571—How Zest Fresh for Managing the Produce Cold Chain Reduces Waste and Saves Retailers Money . . . Beginning on Day One"; https://www.zestlabs.com/downloads/Today-You-Saved.pdf; Jun. 3, 2018; pp. 1-6.

Zest Labs; "True Transparency for Freshness Management, Food Safety, Authenticity and Traceability"; https://www.zestlabs.com/wp-content/uploads/2018/03/30/04/0218-Zest-Fresh-for-Protein-Solution-Overview.pdf; Feb. 4, 2018; pp. 1-2.

Zest Labs; "Zest Labs FAQ and Reference Guide"; https://www.zestlabs.com/downloads/Zest-Labs-FAQ-and-Reference-Guide.pdf; Jul. 1, 2018; pp. 1-6.

Zest Labs; "Zest Labs Professional Services"; https://www.zestlabs.com/wp-content/uploads/2018/03/SO-05-0318-Zest-Labs-Profess ional-Services.pdf; Mar. 5, 2018; pp. 1-2.

Robertson, Gordon L.; "Food Packaging: Principles and Practice"; 3rd Ed.; Boca Raton; CRC Press; 2013; pp. 1-33.

Haard, Norman F., et al.; "Characteristics of Edible Plant Tissues"; Food Chemistry, edited by Owen R. Fennema; 3rd Ed.; Marcel Dekker, Inc.; 1996; pp. 943-1011.

Singh, R. Paul et al.; "Introduction to Food Engineering"; 5th Ed.; Academic Press; 2014; pp. 1-31.

Wells, John H., et al.; "The Application of Time-Temperature Indicator Technology to Food Quality Monitoring and Perishable Inventory Management"; Mathematical Modelling of Food Processing Operations, edited by Stuart Thorne; Elsevier Applied Science; 1992; pp. 1-41.

Labuza, T. P., et al.; "The Relationship Between Processing and Shelf Life"; Foods for the '90s, edited by Gordon G. Birch, et al.; Elsevier Applied Science; Aug. 1, 1990; pp. 1-21.

Kong, F. et al.; "Chemical Deterioration and Physical Instability of Foods and Beverages"; The Stability and Shelf Life of Food, edited by Persis Subramaniam; 2nd Ed.; Woodhead Publishing; 2016; pp. 1-21.

Singh, R. P.; "Scientific Principles of Shelf-Life Evaluation"; Shelf-Life Evaluation of Foods, edited by Dominic Man, et al.; 2nd Ed.; Aspen Publishers, Inc.; 2000; pp. 1-23.

Kader, Adel a., et al .; "Technologies to Extend the Refrigerated Shelf Life of Fresh Fruit"; Food Storage Stability, edited by Irwin A. Taub, et al.; Boca Raton; CRC Press; 1998; pp. 1-27.

Wells, John H. et al.; "Quality Management During Storage and Distribution"; Food Storage Stability, edited by Irwin A. Taub, et al.; Boca Raton; CRC Press; 1998; pp. 1-29.

Wells, John H., et al.; "Temperature Tolerance of Foods during Distribution"; Handbook of Food Engineering Practice, edited by Kenneth J. Valentas, et al.; Boca Raton; CRC Press; 1997; pp. 1-29.

UKIPO; App. No. 1711034.7; Examination Report dated Feb. 20, 2020.

Haugen, John E., et al.; "Application of gas-sensor array technology for detection and monitoring of growth of spoilage bacteria in milk: A model study"; Analytica Chimica Acta; vol. 565, No. 1; https://doi.org/10.1016/j.aca.2006.02.016; Feb. 23, 2006; pp. 10-16.

Kader, Adel A.; "Postharvest Technology of Horticultural Crops"; 2002; 3rd Ed.; University of California Agriculture and Natural Resources; Oakland; 56 pages.

Kader, Adel A.; "Postharvest Technology of Horticultural Crops"; 2002; 3rd Ed.; University of California Agriculture and Natural Resources; Oakland; 74 pages.

Kader, Adel A.; "Postharvest Technology of Horticultural Crops"; 2002; 3rd Ed.; University of California Agriculture and Natural Resources; Oakland; pp. 113-196.

Kader, Adel A.; "Postharvest Technology of Horticultural Crops"; 2002; 3rd Ed.; University of California Agriculture and Natural Resources; Oakland; pp. 197-250.

Kader, Adel A.; "Postharvest Technology of Horticultural Crops"; 2002; 3rd Ed.; University of California Agriculture and Natural Resources; Oakland; pp. 251-314.

Kader, Adel A.; "Postharvest Technology of Horticultural Crops"; 2002; 3rd Ed.; University of California Agriculture and Natural Resources; Oakland; pp. 315-384.

(56) References Cited

OTHER PUBLICATIONS

Kader, Adel A.; "Postharvest Technology of Horticultural Crops"; 2002; 3rd Ed.; University of California Agriculture and Natural Resources; Oakland; pp. 385-434.
Kader, Adel A.; "Postharvest Technology of Horticultural Crops"; 2002; 3rd Ed.; University of California Agriculture and Natural Resources; Oakland; pp. 435-480.
Kader, Adel A.; "Postharvest Technology of Horticultural Crops"; 2002; 3rd Ed.; University of California Agriculture and Natural Resources; Oakland; pp. 67-112.
*Zest Labs, Inc.* v *Walmart*; ECF No. 002; Zest Labs, Inc. et al.; "Motion for Leave to File Complaint Under Seal and to Establish Briefing Schedule Relating to Potentially Confidential Information in Complaint"; United States District Cowl for the Eastern District of Arkansas; Case No. 4:18-CV-00500-JM; Aug. 1, 2018; pp. 1-4.
*Zest Labs, Inc.* v *Walmart*; ECF No. 003; Zest Labs, Inc. et al.; "Brief in Support of Motion for Leave to File Complaint Under Seal and to Establish Briefing Schedule Relating to Potentially Confidential Information Complaint"; United States District Court for the Eastern District of Arkansas; Case No. 4:18-CV-00500-JM; Aug. 1, 2018; pp. 1-4.
*Zest Labs, Inc.* v *Walmart*; ECF No. 035; Walmart; "Defendant's Response to Plaintiffs' Motion for Leave to File Complaint Under Seal"; United States District Court for the Eastern District of Arkansas; Case No. 4:18-CV-00500-JM; Aug. 27, 2018; pp. 1-3.
*Zest Labs, Inc.* v *Walmart*; ECF No. 038; Zest Labs, Inc. et al.; "Plaintiffs' Reply in Support of Plaintiffs' Motion for Leave to File Complaint Under Seal"; United States District Court for the Eastern District of Arkansas; Case No. 4:18-V-00500-JM; Aug. 31, 2018; pp. 1-3.
*Zest Labs, Inc.* v *Walmart*; ECF No. 041; Walmart; "Defendant's Motion for Leave to File Under Seal"; United States District Court for the Eastern District of Arkansas; Case No. 4:18-CV-00500-JM; Sep. 4, 2018; pp. 1-3.
*Zest Labs, Inc.* v *Walmart*; ECF No. 098; Walmart; "Defendant's Brief in Support of Its Motion for Protective Order and to Compel Identification of Alleged Trade Secrets"; United States District Court for the Eastern District of Arkansas; Case No. 4:18-CV-00500-JM; Feb. 11, 2019; pp. 1-29.
*Zest Labs, Inc.* v *Walmart*; ECF No. 101-01; Sammi, P. Anthony; "Exhibit A"; United States District Court for the Eastern District of Arkansas; Case No. 4:18-CV-00500-JM; Feb. 15, 2019; pp. 1-3.
*Zest Labs, Inc.* v *Walmart*; ECF No. 101-02; Tulin, Edward L.; "Exhibit B"; United States District Court for the Eastern District of Arkansas; Case No. 4:18-CV-00500-JM; Feb. 15, 2019; pp. 1-4.
*Zest Labs, Inc.* v *Walmart*; ECF No. 101-03; Tulin, Edward L.; " Exhibit C"; United States District Court for the Eastern District of Arkansas; Case No. 4:18-CV-00500-JM; Feb. 15, 2019; pp. 1-5.
*Zest Labs, Inc.* v *Walmart*; ECF No. 101-04; Zest Labs, Inc. et al.; "Exhibit D Filed Under Seal Pursuant to Order Dated September 7, 2018"; United States District Court for the Eastern District of Arkansas; Case No. 4:18-CV-00500-JM; Feb. 15, 2019; 1 page.
*Zest Labs, Inc.* v *Walmart*; ECF No. 101-05; Zest Labs, Inc. et al.; "Exhibit E Filed Under Seal Pursuant to Order Dated September 7, 2018"; United States District Court for the Eastern District of Arkansas; Case No. 4:18-CV-00500-JM; Feb. 15, 2019; 1 page.
*Zest Labs, Inc.* v *Walmart*; ECF No. 101; Zest Labs, Inc. et al.; "Plaintiffs' Brief in Opposition to Defendant's Motion for Protective Order and to Compel Identification of Trade Secrets"; United States District Court for the Eastern District of Arkansas; Case No. 4:18-CV-00500-JM; Feb. 15, 2019; pp. 1-28.
*Zest Labs, Inc.* v *Walmart*; ECF No. 102-01; Zest Labs, Inc. et al.; "Exhibit A"; United States District Court for the Eastern District of Arkansas; Case No. 4:18-CV-00500-JM; Feb. 20, 2019; pp. 1-28.
*Zest Labs, Inc.* v *Walmart*; ECF No. 102-02; Walmart; "Exhibit B"; United States District Court for the Eastern District of Arkansas; Case No. 4:18-CV-00500-JM; Feb. 20, 2019; pp. 1-59.
*Zest Labs, Inc.* v *Walmart*; ECF No. 102-03; Zest Labs, Inc. et al.; "Exhibit C Filed Under Seal"; United States District Court for the Eastern District of Arkansas; Case No. 4:18-CV-00500-JM; Feb. 20, 2019; 1 page.
*Zest Labs, Inc.* v *Walmart*; ECF No. 102-04; Walmart; "Exhibit D"; United States District Court for the Eastern District of Arkansas; Case No. 4:18-CV-00500-JM; Feb. 20, 2019; pp. 1-10.
*Zest Labs, Inc.* v *Walmart*; ECF No. 102-06; Zest Labs, Inc. et al.; "Exhibit F Filed Under Seal"; United States District Court for the Eastern District of Arkansas; Case No. 4:18-CV-00500-JM; Feb. 20, 2019; 1 page.
*Zest Labs, Inc.* v *Walmart*; ECF No. 102-07; Zest Labs, Inc. et al.; "Exhibit G Filed Under Seal"; United States District Court for the Eastern District of Arkansas; Case No. 4:18-CV-00500-JM; Feb. 20, 2019; 1 page.
*Zest Labs, Inc.* v *Walmart*; ECF No. 102-08; Williams, Fred I.; "Exhibit H"; United States District Court for the Eastern District of Arkansas; Case No. 4:18-CV-00500-JM; Feb. 20, 2019; pp. 1-5.
*Zest Labs, Inc.* v *Walmart*; ECF No. 102-09; Simons, Michael; "Exhibit I"; United States District Court for the Eastern District of Arkansas; Case No. 4:18-CV-00500-JM; Feb. 20, 2019; pp. 1-8.
*Zest Labs, Inc.* v *Walmart*; ECF No. 102-10; Williams, Fred I.; "Exhibit J"; United States District Court for the Eastern District of Arkansas; Case No. 4:18-CV-00500-JM; Feb. 20, 2019; pp. 1-4.
*Zest Labs, Inc.* v *Walmart*; ECF No. 102-11; Simons, Michael; "Exhibit K"; United States District Court for the Eastern District of Arkansas; Case No. 4:18-CV-00500-JM; Feb. 20, 2019; pp. 1-2.
*Zest Labs, Inc.* v *Walmart*; ECF No. 102-12; Tulin, Edward L.; "Exhibit L"; United States District Court for the Eastern District of Arkansas; Case No. 4:18-CV-00500-JM; Feb. 20, 2019; pp. 1-4.
*Zest Labs, Inc.* v *Walmart*; ECF No. 102-13; Sammi, P. Anthony; "Exhibit M"; United States District Court for the Eastern District of Arkansas; Case No. 4:18-CV-00500-JM; Feb. 20, 2019; pp. 1-3.
*Zest Labs, Inc.* v *Walmart*; ECF No. 102-14; Sammi, P. Anthony; "Exhibit N"; United States District Court for the Eastern District of Arkansas; Case No. 4:18-CV-00500-JM; Feb. 20, 2019; pp. 1-3.
*Zest Labs, Inc.* v *Walmart*; ECF No. 102; Zest Labs, Inc. et al.; "Plaintiffs' Motion to Compel Supplemental Responses to Interrogatories and Requests for Production From Defendant"; United States District Court for the Eastern District of Arkansas; Case No. 4:18-CV-00500-JM; Feb. 20, 2019; pp. 1-6.
*Zest Labs, Inc.* v *Walmart*; ECF No. 103; Zest Labs, Inc. et al.; "Plaintiffs' Brief in Support of Motion to Compel Supplemental Responses to Interrogatories and Requests for Production From Defendant"; United States District Court for the Eastern District of Arkansas; Case No. 4:18-CV-00500-JM; Feb. 20, 2019; pp. 1-24.
*Zest Labs, Inc.* v *Walmart*; ECF No. 105-1; Walmart; "Exhibit A—Filed Under Seal Pursuant to Order Dated September 7, 2018"; United States District Court for the Eastern District of Arkansas; Case No. 4:18-CV-00500-JM; Feb. 25, 2019; 1 page.
*Zest Labs, Inc.* v *Walmart*; ECF No. 105; Walmart; "Defendant's Response to Plaintiffs' Motion to Compel"; United States District Court for the Eastern District of Arkansas; Case No. 4:18-CV-00500-JM; Feb. 25, 2019; pp. 1-21.
*Zest Labs, Inc.* v *Walmart*; ECF No. 125; Zest Labs, Inc. et al.; "Plaintiffs' Motion to Compel Defendant Walmart to Comply With the Court's Mar. 6, 2019 Order and Otherwise Produce Technical Discovery"; United States District Court for the Eastern District of Arkansas; Case No. 4:18-CV-00500-JM; Apr. 22, 2019; pp. 1-9.
*Zest Labs, Inc.* v *Walmart*; CF No. 126; Zest Labs, Inc. et al.; "Plaintiffs' Brief in Support of Motion to Compel Defendant Walmart to Comply With the Court's Mar. 6, 2019 Order and Otherwise Produce Technical Discovery"; United States District Court for the Eastern District of Arkansas; Case No. 4:18-CV-00500-JM; Apr. 22, 2019; pp. 1-21.
*Zest Labs, Inc.* v *Walmart*; ECF No. 130-1; Sammi, P. Anthony; "*ZestV. Walmart: Mar. 29, 2019* M. Simons Letter to P. Sammi Re Deficient Production of Technical Documents"; United States District Court for the Eastern District of Arkansas; Case No. 4:18-CV-00500-JM; May 8, 2019; pp. 1-2.

(56) References Cited

OTHER PUBLICATIONS

*Zest Labs, Inc.* v *Walmart*; ECF No. 130-2; Tulin, Edward L.; "*Zest*V. *Walmart: Deposition Notices*"; United States District Court for the Eastern District of Arkansas; Case No. 4:18-CV-00500-JM; May 8, 2019; pp. 1-2.

*Zest Labs, Inc.* v *Walmart*; CF No. 130-3; Simons, Michael; "*Zest*V. *Walmart: Deposition Notices*"; United States District Court for the Eastern District of Arkansas; Case No. 4:18-CV-00500-JM; May 8, 2019; pp. 1-3.

*Zest Labs, Inc.* v *Walmart*; ECF No. 130-4; Walmart; "Exhibit D—Filed Under Seal Pursuant to Order Dated Sep. 7, 2018"; United States District Court for the Eastern District of Arkansas; Case No. 4:18-CV-00500-JM; May 8, 2019; 1 page.

*Zest Labs, Inc.* v *Walmart*; ECF No. 130-5; Simons, Michael; "*Zest Labs*V. *Walmart*—Walmart's Apr. 5, 2019 Production"; United States District Court for the Eastern District of Arkansas; Case No. 4:18-CV-00500-JM; May 8, 2019; pp. 1-2.

*Zest Labs, Inc.* v *Walmart*; ECF No. 130; Walmart; "Defendant's Response to Plaintiffs' Motion to Compel Compliance With the Mar. 6, 2019 Order and Technical Discovery"; United States District Court for the Eastern District of Arkansas; Case No. 4:18-CV-00500-JM; May 8, 2019; pp. 1-26.

*Zest Labs, Inc.* v *Walmart*; ECF No. 131-1; Walmart; "Exhibit A—Filed Under Seal Pursuant to Order Dated Sep. 7, 2018"; United States District Court for the Eastern District of Arkansas; Case No. 4:18-CV-00500-JM; May 8, 2019; 1 page.

*Zest Labs, Inc.* v *Walmart*; ECF No. 131-2; Walmart; "Exhibit B—Filed Under Seal Pursuant to Order Dated Sep. 7, 2018"; United States District Court for the Eastern District of Arkansas; Case No. 4:18-CV-00500-JM; May 8, 2019; 1 page.

*Zest Labs, Inc.* v *Walmart*; ECF No. 131-3; Sammi, P. Anthony; "Re: 4:18-CV-00500-JM *Zest Labs Inc et al*V. *Wal-Mart Inc*"; United States District Court for the Eastern District of Arkansas; Case No. 4:18-CV-00500-JM; May 8, 2019; 1 page.

*Zest Labs, Inc.* v *Walmart*; ECF No. 131-4; Simons, Michael; "Re: 4:18-CV-00500-JM *Zest Labs Inc et al*V. *Wal-Mart Inc*"; United States District Court for the Eastern District of Arkansas; Case No. 4:18-CV-00500-JM; May 8, 2019; 1 page.

*Zest Labs, Inc.* v *Walmart*; ECF No. 131; Walmart; "Defendant's Sur-Reply Brief in Further Opposition to Plaintiffs' Motion to Compel"; United States District Court for the Eastern District of Arkansas; Case No. 4:18-CV-00500-JM; May 8, 2019; pp. 1-21.

*Zest Labs, Inc.* v *Walmart*; ECF No. 250; Walmart; "Defendant's Reply Brief in Support of Its Motion to Exclude Proposed Expert Testimony of Patent Attorney Q. Todd Dickinson"; United States District Court for the Eastern District of Arkansas; Case No. 4:18-CV-00500-JM; Mar. 27, 2020; pp. 1-13.

*Zest Labs, Inc.* v *Walmart*; ECF No. 257-1; Walmart; "Defendant's Surreply in Further Opposition to Zest Labs, Inc.'S Motion for Partial Summary Judgment That Walmart Used and Disclosed Zest'S Information in the Walmart Application"; United States District Court for the Eastern District of Arkansas; Case No. 4:18-CV-00500-JM; Mar. 31, 2020; pp. 1-168.

*Zest Labs, Inc.* v *Walmart*; ECF No. 257-1; Walmart; "Defendant's Surreply in Further Opposition to Zest Labs, Inc.'S Motion for Partial Summary Judgment That Walmart Used and Disclosed Zest's Information in the Walmart Application"; United States District Court for the Eastern District of Arkansas; Case No. 4:18-CV-00500-JM; Mar. 31, 2020; pp. 169-336.

*Zest Labs, Inc.* v *Walmart*; ECF No. 257-1; Walmart; "Defendant's Surreply in Further Opposition to Zest Labs, Inc.'S Motion for Partial Summary Judgment That Walmart Used and Disclosed Zest's Information in the Walmart Application"; United States District Court for the Eastern District of Arkansas; Case No. 4:18-CV-00500-JM; Mar. 31, 2020; pp. 337-342.

*Zest Labs, Inc.* v *Walmart*; ECF No. 257; Walmart; "Defendants Motion for Leave to File Surreply in Further Opposition to Zest Labs, Inc.'s Motion for Partial Summary Judgment That Walmart Used and Disclosed Zest's Information in the Walmart Application"; United States District Court for the Eastern District of Arkansas; Case No. 4:18-CV-00500-JM; Mar. 31, 2020; pp. 1-3.

*Zest Labs, Inc.* v *Walmart*; ECF No. 261-1; Blitzer, Rachel R.; "Declaration of Rachel R. Blitzer Regarding Walmart's Surreply in Further Opposition to Zest Labs, Inc.'s Motion for Partial Summary Judgment That Walmart Used and Disclosed Zest's Information in the Walmart Application"; United States District Court for the Eastern District of Arkansas; Case No. 4:18-CV-00500-JM; Apr. 6, 2020; pp. 1-169.

*Zest Labs, Inc.* v *Walmart*; ECF No. 261-1; Blitzer, Rachel R.; "Declaration of Rachel R. Blitzer Regarding Walmart's Surreply in Further Opposition to Zest Labs, Inc.'s Motion for Partial Summary Judgment That Walmart Used and Disclosed Zest's Information in the Walmart Application"; United States District Court for the Eastern District of Arkansas; Case No. 4:18-CV-00500-JM; Apr. 6, 2020; pp. 170-337.

*Zest Labs, Inc.* v *Walmart*; ECF No. 261; Walmart; "Defendants Surreply in Further Opposition to Zest Labs, Inc.'s Motion for Partial Summary Judgment That Walmart Used and Disclosed Zest's Information in the Walmart Application"; United States District Court for the Eastern District of Arkansas; Case No. 4:18-CV-00500-JM; Apr. 6, 2020; pp. 1-5.

*Zest Labs, Inc.* v *Walmart*; ECF No. 262; Walmart; "Brief in Support of Defendant's Motion for Summary Judgment"; United States District Court for the Eastern District of Arkansas; Case No. 4:18-CV-00500-JM; Apr. 21, 2020; pp. 1-54.

*Zest Labs, Inc.* v *Walmart*; ECF No. 263; Walmart; "Defendants Motion to Exclude Certain Proposed Expert Testimony of Mark Lanning"; United States District Court for the Eastern District of Arkansas; Case No. 4:18-CV-00500-JM; Apr. 21, 2020; pp. 1-6.

*Zest Labs, Inc.* v *Walmart*; ECF No. 264; Walmart; "Brief in Support of Defendant's Motion to Exclude Proposed Expert Testimony of Mark Lanning"; United States District Court for the Eastern District of Arkansas; Case No. 4:18-CV-00500-JM; Apr. 21, 2020; pp. 1-26.

*Zest Labs, Inc.* v *Walmart*; ECF No. 265; Walmart; "Defendants Motion to Exclude Testimony of Damages Expert Stephen L. Becker, Ph.D."; United States District Court for the Eastern District of Arkansas; Case No. 4:18-CV-00500-JM; Apr. 21, 2020; pp. 1-7.

*Zest Labs, Inc.* v *Walmart*; ECF No. 266; Walmart; "Brief in Support of Defendant's Motion to Exclude Testimony of Damages Expert Stephen L. Becker, Ph.D."; United States District Court for the Eastern District of Arkansas; Case No. 4:18-CV-00500-JM; Apr. 21, 2020; pp. 1-22.

*Zest Labs, Inc.* v *Walmart*; ECF No. 267; Walmart; "Defendant'S Response to Zest Labs, Inc.'s Motion for Summary Judgment That Information in Walmart's Patent Application Was Not Generally Known or Readily Ascertainable"; United States District Court for the Eastern District of Arkansas; Case No. 4:18-CV-00500-JM; Apr. 21, 2020; pp. 1-23.

*Zest Labs, Inc.* v *Walmart*; ECF No. 268; Walmart; "Defendants Response to Zest Labs, Inc.'s Motion for Partial Summary Judgment That Walmart Used and Disclosed Zest Labs' Information in the Walmart Applications"; United States District Court for the Eastern District of Arkansas; Case No. 4:18-CV-00500-JM; Apr. 21, 2020; pp. 1-29.

*Zest Labs, Inc.* v *Walmart*; ECF No. 269; Walmart; "Defendant's Response to Plaintiffs' Motion to Exclude Testimony of Walmart's Damages Expert, Dr. William Choi"; United States District Court for the Eastern District of Arkansas; Case No. 4:18-CV-00500-JM; Apr. 21, 2020; pp. 1-17.

*Zest Labs, Inc.* v *Walmart*; ECF No. 270; Walmart; "Defendants Response to Plaintiffs' Motion to Exclude Testimony of Walmart's Technical Expert, Dr. David Dobkin, Ph.D."; United States District Court for the Eastern District of Arkansas; Case No. 4:18-CV-00500-JM; Apr. 21, 2020; pp. 1-13.

*Zest Labs, Inc.* v *Walmart*; ECF No. 271; Walmart; "Defendants Response to Plaintiffs' Motion to Exclude Testimony of Walmart's Technical Expert, Dr. Catherine Adams Hutt, Ph.D."; United States District Court for the Eastern District of Arkansas; Case No. 4:18-CV-00500-JM; Apr. 21, 2020; pp. 1-25.

*Zest Labs, Inc.* v *Walmart*; ECF No. 272; Walmart; "Defendant's Reply Brief in Support of Its Motion to Exclude Testimony of Damages Expert Stephen L. Becker, Ph.D."; United States District

(56) References Cited

OTHER PUBLICATIONS

Court for the Eastern District of Arkansas; Case No. 4:18-CV-00500-JM; Apr. 21, 2020; pp. 1-22.
Zest Labs, Inc. v Walmart; ECF No. 273; Walmart; "Defendants Reply Brief in Support of Its Motion for Summary Judgment"; United States District Court for the Eastern District of Arkansas; Case No. 4:18-CV-00500-JM; Apr. 21, 2020; pp. 1-56.
Zest Labs, Inc. v Walmart; ECF No. 274; Walmart; "Defendants Reply Brief in Support of Its Motion to Exclude Proposed Expert Testimony of Mark Lanning"; United States District Court for the Eastern District of Arkansas; Case No. 4:18-CV-00500-JM; Apr. 21, 2020; pp. 1-22.
Zest Labs, Inc. v Walmart; ECF No. 275; Zest Labs, Inc. et al.; "Zest Labs Inc.'s Motion for Partial Summary Judgment That Walmart Used and Disclosed Zest's Information in the Walmart Applications"; United States District Court for the Eastern District of Arkansas; Case No. 4:18-CV-00500-JM; Apr. 21, 2020; pp. 1-4.
Zest Labs, Inc. v Walmart; ECF No. 276; Zest Labs, Inc. et al.; "Plaintiffs' Motion to Exclude Testimony of Walmart's Expert, Dr. David P. Dobkin"; United States District Court for the Eastern District of Arkansas; Case No. 4:18-CV-00500-JM; Apr. 21, 2020; pp. 1-3.
Zest Labs, Inc. v Walmart; ECF No. 277; Zest Labs, Inc. et al.; "Brief in Support of Plaintiffs' Motion to Exclude the Testimony of Walmart's Expert Witness, Dr. David P. Dobkin"; United States District Court for the Eastern District of Arkansas; Case No. 4:18-CV-00500-JM; Apr. 21, 2020; pp. 1-59.
Zest Labs, Inc. v Walmart; ECF No. 278; Zest Labs, Inc. et al.; "Plaintiffs' Motion to Exclude Testimony of Walmart Expert, Dr. Catherine Adams Hutt"; United States District Court for the Eastern District of Arkansas; Case No. 4:18-CV-00500-JM; Apr. 21, 2020; pp. 1-4.
Zest Labs, Inc. v Walmart; ECF No. 279; Zest Labs, Inc. et al.; "Brief in Support of Plaintiffs' Motion to Exclude the Testimony of Walmart's Expert Witness, Dr. Catherine Adams Hutt"; United States District Court for the Eastern District of Arkansas; Case No. 4:18-CV-00500-JM; Apr. 21, 2020; pp. 1-64.
Zest Labs, Inc. v Walmart; ECF No. 280; Zest Labs, Inc. et al.; "Zest Labs Inc.'s Motion for Partial Summary Judgment That Information in Walmart's Patent Application Was Not Generally Known or Readily Ascertainable"; United States District Court for the Eastern District of Arkansas; Case No. 4:18-CC-00500-JM; Apr. 21, 2020; pp. 1-4.
Zest Labs, Inc. v Walmart; ECF No. 281; Zest Labs, Inc. et al.; "Plaintiffs' Motion to Exclude Testimony of Walmart's Damages Expert, Dr. William Choi"; United States District Court for the Eastern District of Arkansas; Case No. 4:18-CV-00500-JM; Apr. 21, 2020; pp. 1-4.
Zest Labs, Inc. v Walmart; ECF No. 282; Zest Labs, Inc. et al.; "Plaintiffs' Brief in Support of Motion to Exclude Testimony of Walmart's Damages Expert, Dr. William Choi"; United States District Court for the Eastern District of Arkansas; Case No. 4:18-CV-00500-JM; Apr. 21, 2020; pp. 1-30.
Zest Labs, Inc. v Walmart; ECF No. 283; Zest Labs, Inc. et al.; "Zest Labs Inc.'s Brief in Support of Its Motion for Partial Summary Judgment That Information in Walmart's Patent Application Was Not Generally Known or Readily Ascertainable"; United States District Court for the Eastern District of Arkansas; Case No. 4:18-CV-00500-JM; Apr. 21, 2020; pp. 1-159.
Zest Labs, Inc. v Walmart; ECF No. 284; Zest Labs, Inc. et al.; "Zest Labs Inc.'s Brief in Support of Its Motion for Partial Summary Judgment That Walmart Used and Disclosed Zest Labs' Information in the Walmart Applications"; United States District Court for the Eastern District of Arkansas; Case No. 4:18-CV-00500-JM; Apr. 21, 2020; pp. 1-165.
Zest Labs, Inc. v Walmart; ECF No. 285; Zest Labs, Inc. et al.; "Zest Labs Inc.'s Motion for Summary Judgment on Its Claim for Breach of Contract"; United States District Court for the Eastern District of Arkansas; Case No. 4:18-CV-00500-JM; Apr. 21, 2020; pp. 1-3.
Zest Labs, Inc. v Walmart; ECF No. 286; Zest Labs, Inc. et al.; "Zest Labs Inc.'s Brief in Support of Its Motion for Summary Judgment on Its Claim for Breach of Contract"; United States District Court for the Eastern District of Arkansas; Case No. 4:18-CV-00500-JM; Apr. 21, 2020; pp. 1-30.
Zest Labs, Inc. v Walmart; ECF No. 287; Zest Labs, Inc. et al.; "Plaintiffs' Response to Defendant's Motion for Summary Judgment"; United States District Court for the Eastern District of Arkansas; Case No. 4:18-CV-00500-JM; Apr. 21, 2020; pp. 1-138.
Zest Labs, Inc. v Walmart; ECF No. 288; Zest Labs, Inc. et al.; "Plaintiffs' Opposition to Defendant's Motion to Exclude Testimony of Damages Expert Stephen L. Becker, Ph.D."; United States District Court for the Eastern District of Arkansas; Case No. 4:18-CV-00500-JM; Apr. 21, 2020; pp. 1-63.
Zest Labs, Inc. v Walmart; ECF No. 289; Zest Labs, Inc. et al.; "Plaintiffs' Brief in Opposition of Defendant's Motion to Exclude Proposed Expert Testimony of Patent Attorney Q. Todd Dickinson"; United States District Court for the Eastern District of Arkansas; Case No. 4:18-CV-00500-JM; Apr. 21, 2020; pp. 1-180.
Zest Labs, Inc. v Walmart; ECF No. 290; Zest Labs, Inc. et al.; "Plaintiffs' Brief in Opposition of Defendant's Motion to Exclude Proposed Expert Testimony of Mark Lanning"; United States District Court for the Eastern District of Arkansas; Case No. 4:18-CV-00500-JM; Apr. 21, 2020; pp. 1-62.
Zest Labs, Inc. v Walmart; ECFNo. 291; Zest Labs, Inc. et al.; "Zest Labs Inc.'s Reply Brief in Support of Its Motion for Partial Summary Judgment That Information in Walmart's Patent Application Was Not Generally Known or Readily Ascertainable"; United States District Court for the Eastern District of Arkansas; Case No. 4:18-CV-00500-JM; Apr. 21, 2020; pp. 1-18.
Zest Labs, Inc. v Walmart; ECF No. 292; Zest Labs, Inc. et al.; "Plaintiffs' Reply in Support of Their Motion to Exclude Testimony of Walmart's Damages Expert Dr. William Choi"; United States District Court for the Eastern District of Arkansas; Case No. 4:18-CV-00500-JM; Apr. 21, 2020; pp. 1-20.
Zest Labs, Inc. v Walmart; ECF No. 293; Zest Labs, Inc. et al.; "Brief in Support of Plaintiffs' Motion to Exclude the Testimony of Walmart's Expert Witness, Dr. David P. Dobkin"; United States District Court for the Eastern District of Arkansas; Case No. 4:18-CV-00500-JM; Apr. 21, 2020; pp. 1-13.
Zest Labs, Inc. v Walmart; ECF No. 294; Zest Labs, Inc. et al.; "Zest Labs Inc.'s Reply in Support of Their Motion for Partial Summary Judgment That Walmart Used and Disclosed Zest's Information in the Walmart Application"; United States District Court for the Eastern District of Arkansas; Case No. 4:18-CV-00500-JM; Apr. 21, 2020; pp. 1-39.
Zest Labs, Inc. v Walmart; ECF No. 295; Zest Labs, Inc. et al.; "Plaintiffs' Reply in Support of Their Motion to Exclude the Testimony of Walmart's Expert Witness, Dr. Catherine Adams Hutt"; United States District Court for the Eastern District of Arkansas; Case No. 4:18-CV-00500-JM; Apr. 21, 2020; pp. 1-23.
Zest Labs, Inc. v Walmart; ECF No. 296; Zest Labs, Inc. et al.; "Plaintiffs' Objections to and Motion to Strike Evidence Cited in Walmart's Responses to Zest Labs, Inc.'s Statement of Material Facts in Support of Its Motions for Partial for Summary Judgement and Motion for Summary Judgment"; United States District Court for the Eastern District of Arkansas; Case No. 4:18-CV-00500-JM; Apr. 21, 2020; pp. 1-5.
Zest Labs, Inc. v Walmart; ECF No. 297; Zest Labs, Inc. et al.; "Plaintiffs' Memorandum in Support of Objections to and Motion to Strike Evidence Cited in Walmart's Responses to Zest Labs, Inc.'s Statement of Material Facts in Support of Its Motions for Partial for Summary Judgement and Motion for Summary Judgment"; United States District Court for the Eastern District of Arkansas; Case No. 4:18-CV-00500-JM; Apr. 21, 2020; pp. 1-5.
Zest Labs, Inc. v Walmart; ECF No. 298; Walmart; "Defendant's Consolidated Brief in Opposition to Plaintiffs' Objections to and Motions to Strike Evidence Cited by Walmart in Connection With Summary Judgment Motions"; United States District Court for the Eastern District of Arkansas; Case No. 4:18-CV-00500-JM; May 4, 2020; pp. 1-18.

* cited by examiner

SYSTEM AND METHOD FOR MONITORING GAS EMISSION OF PERISHABLE PRODUCTS

RELATED APPLICATION(S)

This application is a continuation of U.S. application Ser. No. 15/541,160 filed Jun. 30, 2017, which is a 35 U.S.C. 371 national stage application of International Application No. PCT/US2015/067902 filed Dec. 29, 2015, which claims the benefit of U.S. Provisional Application No. 62/098,948, filed Dec. 31, 2014, all of which are incorporated by reference in their entireties.

TECHNICAL FIELD

This invention relates generally to retail sales and perishable products.

BACKGROUND

Management of fresh products is an important component of retail grocery management. With the growth of e-commerce, fresh products may become one of the main draws for shoppers to visit brick and mortar retail locations. Therefore, the success of fresh product management can heavily impact the success of the entire retail grocery operation. However, fresh products possess a special challenge in inventory management due to their perishable nature. Many factors throughout a product's supply, distribution, and retail stages can affect the freshness of the product when it arrives in the hands of a customer.

BRIEF DESCRIPTION OF THE DRAWINGS

Disclosed herein are embodiments of system, method and apparatuses for automatically monitoring merchandise in a retail sales environment. This description includes drawings, wherein.

Figure 1:
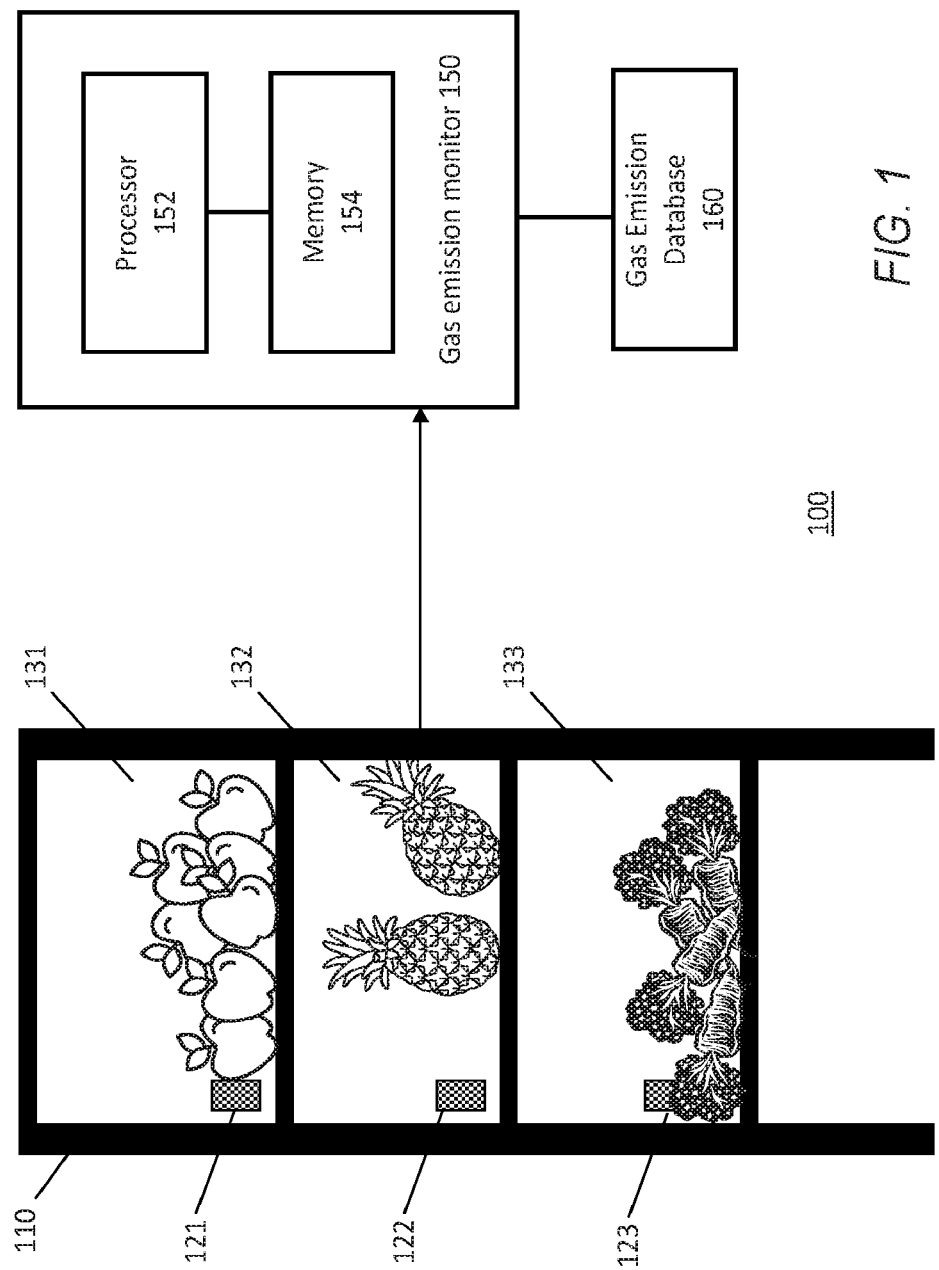
FIG. 1 is a diagram of a system in accordance with several embodiments.

Elements in the features are illustrated for simplicity and clarity and have not necessarily been drawn to scale. For example, the dimensions and/or relative positioning of some of the elements in the figures may be exaggerated relative to other elements to help improve understanding of various embodiments of the present invention. Also, common but well-understood elements that are useful or necessary in a commercially feasible embodiment are often not depicted in order to facilitate a less obstructed view of these various embodiments of the present invention. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein.

DETAILED DESCRIPTION

Generally speaking, pursuant to various embodiments, systems, apparatuses and methods are provided herein for monitoring a gas emission of products on a display fixture.

The storage and transportation of perishable goods are often rigorously tracked and logged to ensure the goods are in desired condition when they arrived at a retail location. However, conventionally, systems, technologies and processes provide minimal visibility to product freshness and placement at store level. Supply chain data provides visibility to when product is received at the store, but there is very limited visibility to where product is placed in the store (e.g. in the backroom, on the sales floor, etc.), whether or not the product has been kept within the appropriate temperature standards and the amount of lifespan remaining when the would be considered suitable for consumption. When a fresh product is kept out of appropriate temperature standards the effective lifespan before the product spoils is reduced. Variations in lifespan may also occur due to variation in product varieties and picking conditions. While this loss of product lifespan is frequently not visible on the product, it does change the gas emissions that come from the product. Improper handling of fresh product can lead customers inadvertently purchasing products that will spoil shortly after they are acquired. The inexperience of associates who work in fresh products department can also pose challenges to operational execution at store level. Smart fixtures could be used not only to evaluate the freshness level of product in store, but could also provide visibility to where products were in the store, and could provide real time data that could be used for price management (by identifying when a freshness based markdown on a collection of products was appropriate) and to create tasks for fresh area associates based on store specific fresh circumstances.

Embodiments of the disclosed system would add gas emission sensors to fixtures used to display fresh product. The sensors would measure the gas emissions from the product/s displayed on the fixture. In some cases, each fixture may include a small computing device (e.g. a microprocessor or a RASPBERRY PI type device) that would be WiFi enabled.

In general terms, some embodiments provide a system for automatically monitoring merchandise in a retail sales environment is provided. The system includes a display fixture configured to store and display for sale a group of perishable items and one or more gas emission sensors associated with the display fixture and configured to measure gas emissions from the group of perishable items. The system further includes a control circuit coupled to the one or more gas emission sensors and configured to receive a gas emission measurement taken at the display fixture, compare the gas emission measurement with stored gas emission data associated with a category of the group of perishable items; and make a determination corresponding to the group of perishable items based on the comparison.

In order to match sensor measurements of product freshness with product gas emission outputs, a database of gas emissions across product lifecycle may be used. A profile of each individual fresh product to be considered may be included or added to the system. Variations could include hand held units that measure fresh product gas emissions and or spectrometers that take measures from light producing sensors.

Referring now to FIG. 1, a system for providing a gas emission monitoring is shown. The system 100 includes a display fixture 110 having gas sensors 121, 122, and 123 in communication with a gas emission monitor 150. The display fixture 110 may be a compartment shelf as shown 110 or a table, a refrigerated case, a stand, and the like. Additional examples of display fixtures are provided herein with reference to FIGS. 5-6 below. Generally, the display fixture 110 may be any fixture on the sales floor having any number of compartments that stores and displays products to customers for purchase. Generally, the sales floor of a typical retailer selling perishable products is a relatively uncontrolled and open environment where there are fluctuations in air flow, temperature, humidity, light exposure and moisture in any one area over time and between different areas of the sales floor. This is in contrast to more controlled environments involved in other portions of the supply chain, e.g., in distribution centers or delivery vehicles and refrigerated stock rooms. The retail sale floor is open to allow customers to move therethrough. Air flow from the outside environment can affect perishable products differently in different portions of the floor, such as those portions closer to open doorways and sky lights.

The display fixture 110 includes gas sensors 121, 122, and 123 for monitoring compartments 131, 132, and 133, respectively. A compartment may generally be described as a display area defined between dividers, such as a shelf, a bin, a rack, etc. In some embodiments, a gas sensor may gather gas emission from an unconfined area or space of a display fixture. While one gas sensor is shown in each of the compartments of the display fixture 110 in FIG. 1, each compartment may include a set of any number of sensors. The sensors may also be located in different areas of the compartment. The gas sensors 121, 122, and 123 may be configured to measure any gas released by the perishable item during ripening and/or decay. For example, the gas sensors 121, 122, and 123 may measure one or more of ethylene, ammonia, acetylene, nitrogen, carbon dioxide, oxygen. In some embodiments, the sensors may be selected based on the type of perishable item they are intended to measure. In some embodiments, the display FIG. 110 may be equipped with other sensors such as temperature moisture, and weight sensors to supplement the data collected by the gas sensors 121, 122, and 123. In some embodiments, the display fixture may further include a microprocessor and/or a communication module for communicating the data gathered by the sensor to the gas emission monitor 150. The communication may be via one or more of WiFi, long or short range radio frequency communication channel, wired connection, local area network, the Internet, and the like.

Each compartment of the display fixture 110 may contain a different type of product. For example, in FIG. 1, compartment 131 contains apples, compartment 132 contains pineapples, and compartment 133 contains carrots. The sensor(s) 121, 122, and 123 associated with each of the compartments 131, 132, and 133 are configured to collect gas emission measurement data from the items in the compartment. For example, gas sensor 121 is configured to read the collective gas emission of any and all apples in compartment 131. While fruits are shown in FIG. 1, the compartments 131, 132, and 133 may be used to hold any type of perishable item such as produce, dairy, meat, seafood, plant, floral, bakery goods, deli and prepared meals etc. Generally, the gas sensors may be used to monitor any perishable food or non-food item that releases gas without departing from the spirit of the present disclosure.

The gas emission monitor 150 receives the gas emission measurement from the gas sensors 121, 122, and 123. The gas emission monitor 150 may be one or more a computing device attached to the display fixture 110, a local computing device located in the same premise as the display fixture 110, or a remote computing device. The gas emission monitor 150 may be generally described as a control circuit and may be any processor based computing device such as a personal computer (PC), a portable device, a server, a cloud computing device, etc. In some embodiments, the functionalities of the gas emission monitor 150 described herein may be performed by two or more separately implemented computing devices. The gas emission monitor 150 may include a processor 152 and a memory 154.

The processor 152 may be configured to compare the gas emission measurements from the gas sensors 121, 122, and 123 with gas emission data from stored in a gas emission database 160. The comparison is described in more detail below with reference to FIGS. 2-4 below. The gas emission monitor 150 may further include or be accessible by user interface devices for a user to interact with the collected gas emission data.

The memory 154 may store a set of instructions executable by the processor to process the data collected from the gas sensors 121 as described with reference to FIGS. 2-4. The memory 154 may further store a history of gas sensor readings. For example, the gas sensor 122 may be configured to take a gas measurement every 10 minutes, and the memory 154 may store a log of such readings. The memory 154 may further store other data used in analyzing the gas emission data such as a store's planogram, a store's inventory information, product throughput data, projected sales data, product usage information etc. Planograms generally refers to a schematic or a floor plan that defines where and when products should be placed on each shelving unit of a retail space.

The gas emission database 160 may store a plurality of gas emission profiles, each profile being associates with one or more of a genus, a species, a variety, a cultivar, a growth location, and a growth time of a perishable product. For example, a profile may be associated with Gala apples, and a separate profile may be associated with Fuji apples. In another example, different profiles may be associated with Gala apples grown in California Central Valley and in Northern New Zealand. In yet another example, Chandler strawberries grown organically in southern California may have a different profile from Chandler strawberries grown conventionally in the same region. Each gas emission profile may be based on studies of the particular product category's typical gas emission during ripening and decay. In some embodiments, a gas emission profile may be a chart of the typical amount of ethylene released by a perishable product as it ripens and/or decays. In some embodiments, a profile may include emission data of two or more gasses. Each profile may be uniquely associated with a category and may be made based on studies and experiments performed on other items of the same category. For example, a profile for Gala apples may be generated by measuring the gas emission of one or more groups of Gala apples shortly after harvest until expiration under a controlled environment or in a retail environment. In some embodiments, data collected by the gas sensors 121, 122, and 123 in a retail environment are added to the data in the gas emission database to generate and/or supplement gas emission profiles for later use. The gas emission database 160 may be integrated, separately implemented, local, and/or remote from the memory 154 of the gas emission monitor 150.

By comparing the gas emission reading from the display fixture 110 and the stored gas profile, the processor 152 may estimate the freshness and/or the remaining shelf life of the perishable item. For example, the processor 152 may estimate a best-by date and/or an expiration date for the item. In some embodiments, the profile may indicate a mixture of gasses that can be used to identify the perishable product. For example, gas sensors 121, 122, and 123 may detect a mixture of two or more gasses in a compartment and the processor is able to determine what type of item is in the compartment based on the presence and/or constitution of the one or more detected gases.

While only one display fixture 110 and one gas emission monitor 150 is shown in FIG. 1, a monitoring system may include any number of display fixtures and gas emission monitors sharing sensor measurements and/or stored gas emission data.

In some embodiments, the sensors would communicate the type of product that is displayed on the fixture, the length of time that the product had been on the fixture, and the expected life span remaining on the product on the fixture. This information may be sent to store or cloud based servers, from which specific actions could be determined. Examples of the types of decisions that include: identifying product that has been received in the store, but has not been put on the sales floor, identifying product that is nearing spoilage and should be marked down to facilitate rapid sale, identifying product that should have been sold through to make space for arriving new products that are intended to be placed where the existing products are remaining and identifying compliance of fixture product with assigned floor plan. The system could be implemented with fresh display fixtures that include sensors and WiFi, Bluetooth, NFC, or wired communication enabled computing devices. Existing fixtures may also be retrofitted to include gas emissions sensors.

Figure 2:
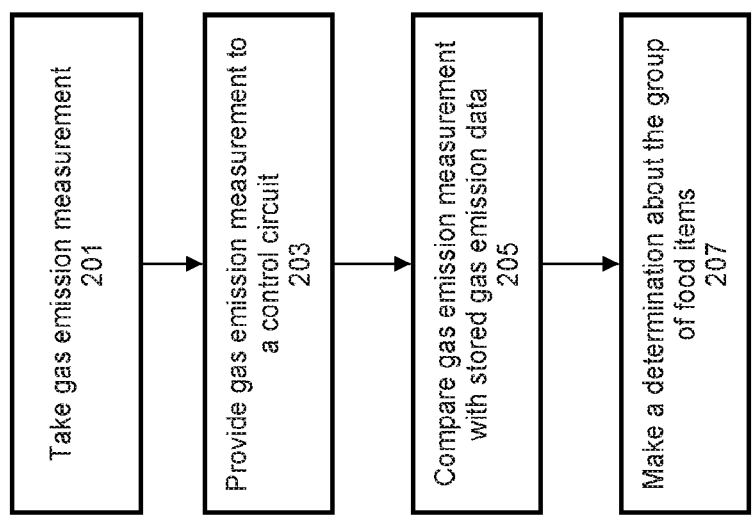
FIG. 2 is a flow diagram of a method in accordance with several embodiments.

Referring now to FIG. 2, a method of monitoring merchandise in a retail environment is shown. The method shown in FIG. 2 may be performed by the system shown in FIG. 1 or any system including one or more control circuits, such as computing devices, processor-based devices, and the like.

In step 201, gas emission is taken at a display fixture with one or more gas sensors. The gas sensors may be attached to a display fixture or be integrated into the structure of the display fixture that is configured to stores and displays for sale a group of perishable items. The gas sensors are configured to measure the gas emission of any item within an area, such as a compartment, section or shelf, of the display fixture. For example, the gas emission measurement may be of all the apples in a bin, all the cabbage between two dividers, etc. In some embodiments, two or more different gasses are measured by sensors in step 201. In some embodiments, step 201 is repeated periodically to provide history of the perishable item's gas emission to a control circuitry.

In step 203, the gas emission measurement taken in step 201 is provided to a control circuitry. The control circuit may be one or more of a computing device attached to or near the display fixture, a computing device in the same retail establishment as the display fixture, or a remote computing device. For example, the sensor data may be provided to a cloud-based server or a local computer for analysis. The gas emission measurement may be communicated to the gas emission monitor via a wired or wireless connection.

In step 205, the control circuit compares the measured gas emission with stored gas emission data. In some embodiments, a category associated with the measured perishable items is first determined. For example, the control circuit may match the gas emission measurement with one of a plurality of possible categories based on the type and the constitution of the gas(es) detected. In addition to data related to the gas(es collected directly from the sensors, data regarding the past, present and future product included for the display unit, as well as current inventory information within the store may be utilized as a means to determine the type of product that the sensors detect. In some embodiments, the category may be determined based on the location of the sensor and a store planogram. For example, the location of the sensor may be matched with the designated location of an item. In some embodiments, the category of the item may be provided by other sensors such as a radio frequency identification (RFID) reader or a barcode scanner. The category of the group of perishable items may correspond to one or more of a genus, a species, a variety, a cultivar, a growth location, and a growth time of the item. The comparison may be based on comparing a history of the item's current gas emission with an emission over time profile of the matching category. For example, the control circuit may determine which point of the emission curve of the profile best matches the measured item's current condition based on the type and/or concentration of the detected gas. In some embodiments, the stored gas emission data may be one or more threshold values. For example, the stored gas emissions data may be one or more values of ethylene concentration corresponding to one or more stages of the item's ripening and/or decay. The threshold values may correspond to different actions to be taken, for example, there may be threshold values for level one discount, level two discount, and discard. In some embodiments, a history of gas emission reading is compared to the stored emission profile. For example, the rate of change in the measured gas emission over time (for example, last 3 hours, last day) may be compared to the rate of change in a stored profile to determine the freshness of the product.

In step 207, the control circuit makes a determination about the group of perishable items. The determination may be one or more of: estimated freshness, estimated expiration date, item presence, item location, and item type. In some embodiments, the determination may be whether the correct item is present in the correct location. For example, based on shipment delivery information, the control circuit may expect strawberries to be in a compartment associated with a sensor and determine whether strawberries are indeed present based on whether the measurements taken by the gas sensor matches known range of gas emission of strawberries. In some embodiments, control circuit may determine the remaining lifespan of the item. The gas measurement may be compared to stored gas emission data to determine an estimated expiration date of the item. For example, as described in step 205, the concentration of one or more measured gases may be compared with stored gas emission data to determine which stage of ripening and/or decay best match the measured item. The expiration date generally refers to the best-by date and/or the date that the food item becomes undesirable or unsafe for use or consumption.

In some embodiments, the control circuit furthers determines whether to apply a discount to the group of perishable items based on the determination. For example, if the item is about to expire, the store may apply a discount to the item to try to increase the sales rate of the item. In some embodiments, the determination may further take into account a forecasted rate of sales, an expected time between purchase and use by a customer, and incoming inventory information. For example, if an item still has 10 days until expiration but is not expected to be used by users until 7 days after purchase, the system may price the item to sell through within 3 days. In some embodiments, if the item still has 10 days of lifespan until expiration but another product that will occupy the same space is scheduled to arrive in 5 days, the system my price the item to sell through within 5 days. In some embodiments, different levels of discount may be applied based on the estimated proximity of the expiration date.

Figure 3:
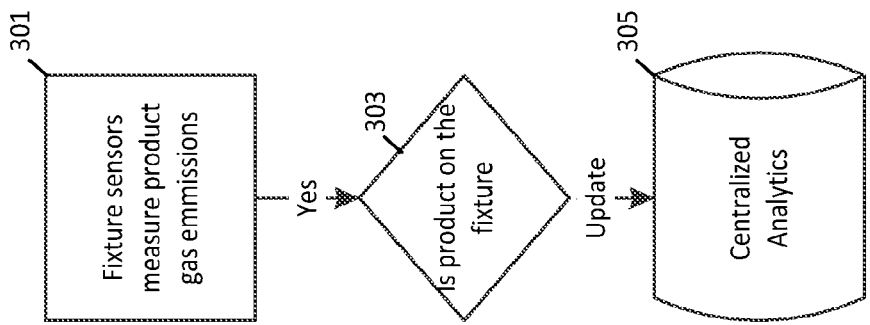
FIG. 3 is a flow diagram of a general process in accordance with several embodiments.

Now referring to FIG. 3, a process for determining whether a product is on the fixture is shown. In step 301, fixture sensor measure product gas emission. The fixture sensor may be configured to measure gas emission of items in an area of the fixture. In some embodiments, step 301 may be similar to step 201 of FIG. 2. In step 303, the system determines whether the product is on the fixture. Product may generally refer to any perishable merchandise in a retail environment such as produce, meat, and diary. Fixture may generally refer to any storage and display fixtures on the retail floor, such a table, a shelf, a rack, a refrigerator and the like. In some embodiment, the system determines whether any product is on the fixture. In some embodiments, the system determines whether the detected gas emission matches what is supposed be on the fixture. In some embodiments, the system is configured to identify the product based on the gas emission measure. After step 303, the determined information from step 303 is sent to a centralized analytics database 305 for storage and further utilization. For example, the data in the centralized analytics database 305 may be used to determine whether the store's planogram is being followed. The data may also be used to verify the product throughput and/or determine whether discount should be applied to one or more products. Centralized data may also be used to provide chain wide visibility to product decomposition rates, allowing for enhanced supply chain planning from agricultural production to retail sale.

Figure 4:
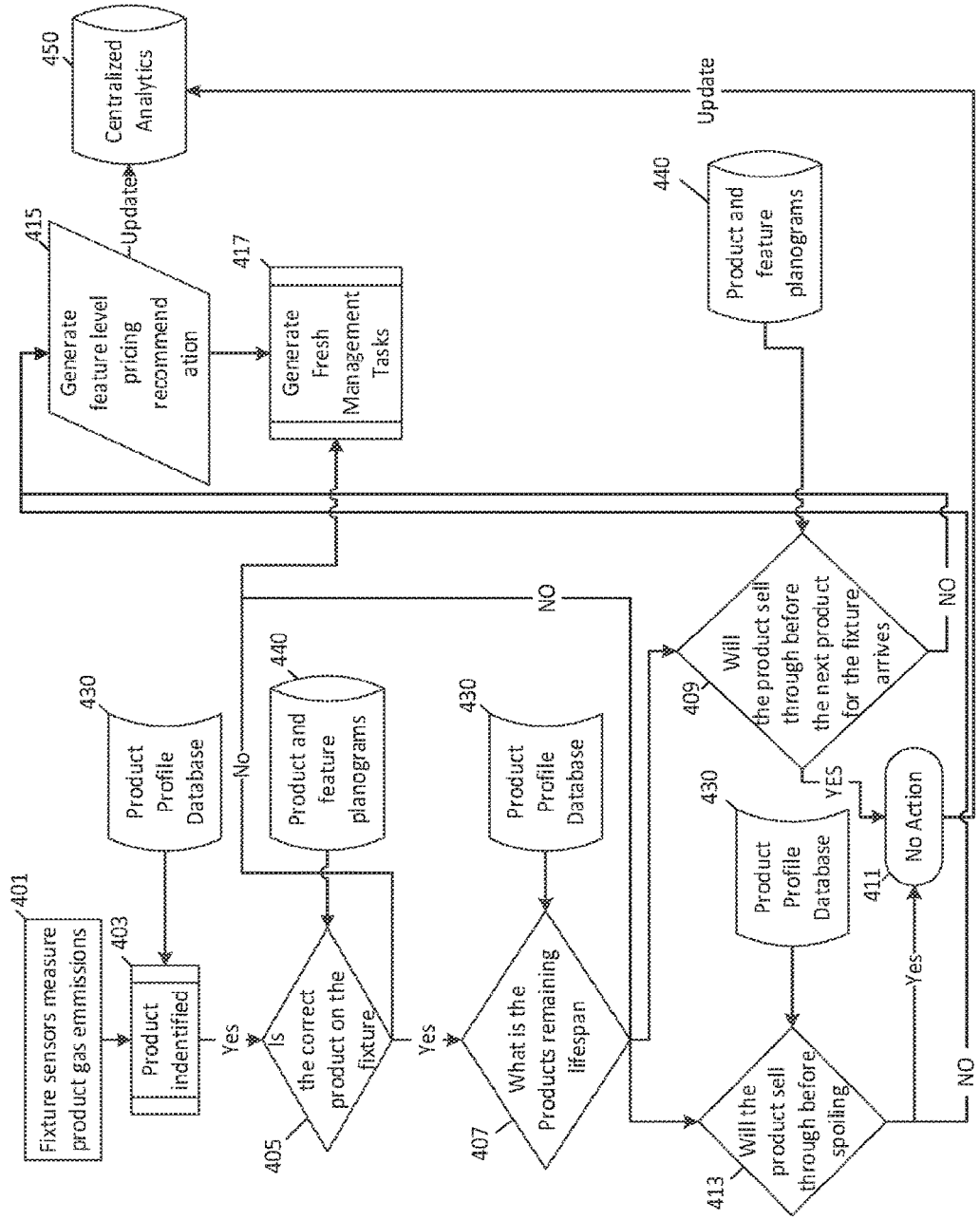
FIG. 4 is a flow diagram of a process in accordance with several embodiments.

Now referring to FIG. 4, a process for monitoring perishable products is shown. The method shown in FIG. 4 may be performed by the system shown in FIG. 1 or any system including one or more control circuitry, computing device, processor-based device, and the like.

in step 401, fixture sensors measure product gas emission of any product in a space of the display fixture associated with the sensor. In step 403, the product is identified. The identification of the product may be based on information stored in a product profile database 430. For example, the measured gas emission may be compared to several gas emission profiles to find a match. When the product is identified, in step 405, the system determines whether the correct product is on the fixture. Step 405 may be based on information in the product and feature planograms database 440. For example, the system may determine whether the identified product matches the intended product at the location of the sensor based on the planograms of the store. If the product on the fixture does not match the planogram, the process may move to step 417 to generate a fresh management task. For example, a task may be that a store clerk should remove the incorrect product and/or place the correct product on the fixture.

In step 407, the system determines the product's remaining lifespan. The determination may be based on comparing the sensor measurements with stored gas emission data in the product profile database 430. The system may compare the current gas emission and match it to a data point in a stored gas emission profile to determine the remaining lifespan. In step 413, the system determines whether the product will sell through before spoiling. If the product will sell through, no action is taken in step 411. If the product is not expected to sell through by the expiration date, the process moves to step 415 and a feature level pricing recommendation is generated. The pricing recommendation would be applied to the entire group of products, for example, all Gala apples on the sales floor. The pricing recommendation is set at a level such that the estimated sell through date would be before the spoiling date. In some embodiments, the targeted sell through date may be modified based on usage habit information. For example, if customers typically do not cook a potato until at least five days after purchase, the targeted sell through date may be set at 5 or more days before the estimate spoilage date. The pricing recommendation may be set according to such adjustment.

After step 407, the system may also determine whether the product will sell through before the next product for the fixture arrives in step 409. Step 409 may be based on information in the product and feature planograms database 440. For example, the arrival of the next product for the fixture may be provided in the inventory and shipment information stored in the product and feature planograms database 440. If the product is expected to sell through prior to the arrival of the next product, no action is taken in step 411. If the product is not expected to sell through prior to the arrival of the next product, the process proceeds to step 415 and a feature level pricing recommendation is generated to increase the sales rate of the product to make space for the incoming product.

After a pricing recommendation is generated in step 415, a fresh management task is generated in step 417. The management task may include one or more of reviewing and approving the pricing recommendation, replacing signage, relocating product, generating an advertisement, and the like. In some embodiments, the fresh management task may be performed automatically by the system, manually by a retail worker, or by a combination of the two.

After a pricing recommendation is generated at 415 or no action is taken at step 411, the collected data and determinations are stored into a centralized analytics database 405. The information stored in the centralized analytics database 405 may be used to generate reports to help the retail store plan future planograms, set future prices, determine selection and orders for new products, forecast sales rates, and the like. In some embodiments, the centralized analytics information may be shared with farmer, producers, and shipper for the development of new products and procedures to improve the freshness of the products. In some embodiments, the data in the centralized analytics database 450 may also be used to update the information in the product profile database 430 and the product and feature planograms database 440 for further use.

The product profile database 430, the product and feature planograms database 440, and the centralized analytics database 450 may each be implemented in one or more physical devices and may be local or remote from the system described FIG. 1. One of more of these databases may be local to each retail location, shared among a geographical region, and/or shared among an entire organization or company.

Figure 5:
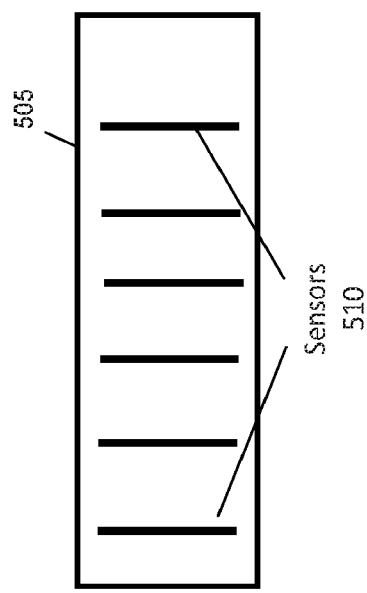

Now referring to FIG. 5, a display shelf 505 with a sensor array 510 is shown. The sensor array 510 may be placed at any portion of the fixture, including horizontal portion and/or the vertical portion of the display shelf 505. Each of the sensors in the sensor array 510 may be configured to measure the same type of gas(es) or different gasses. The sensors 510 may be attached and/or integrated into the structure of the display shelf 505. For example, the sensors may be imbedded into the shelf such that the surface of the shelf is even for storing and displaying the perishable products. Now referring to FIG. 6, a display table 605 with sensors 610 is shown. In FIG. 5, the sensors 610 are positioned diagonally in the four squadrons of the horizontal surface of a rectangular display table 605.

Figure 6:
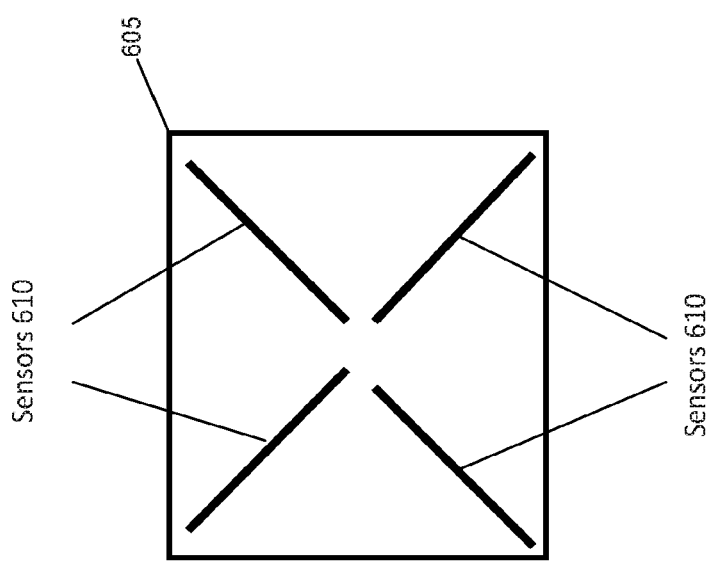
FIGS. 5-6 are illustrations of sensor layout on display units in accordance with several embodiments.

FIGS. 5 and 6 are provided as examples of possible sensor layout. Generally, gas sensors may be attached or integrated with display fixtures in any configuration that is able to measure gas emission from products stored and displayed on the fixture without departing from the spirit of the present disclosure.

In some embodiments, a system for automatically monitoring merchandise in a retail sales environment is provided. The system includes a display fixture configured to store and display for sale a group of perishable items and one or more gas emission sensors associated with the display fixture and configured to measure gas emissions from the group of perishable items. The system further includes a control circuit coupled to the one or more gas emission sensors and configured to receive a gas emission measurement taken at the display fixture, compare the gas emission measurement with stored gas emission data associated with a category of the group of perishable items; and make a determination corresponding to the group of perishable items based on the comparison.

In some embodiments, a method for automatically monitoring merchandise in a retail sales environment is provided. The method includes taking, at a display fixture, a gas emission measurement with one or more gas emission sensors associated with the display fixture, the display fixture configured to store and display for sale the group of perishable items, providing the gas emission measurement to a control circuit, comparing, by the control circuit, the gas emission measurement with stored gas emission data associated with a category of the group of perishable items, and making, by the control circuit, a determination corresponding to the group of perishable items based on the comparing.

In some embodiments, an apparatus for automatically monitoring merchandise in a retail sales environment is provided. The apparatus includes a control circuit, and a non-transitory computer readable memory storing a set of instructions executable by the control circuit. The instructions executable by the control circuit being configured to cause the control circuit to perform the steps of: receive a gas emission measurement measured with one or more gas emission sensors associated with a display fixture configured to store and display for sale a group of perishable items, compare the gas emission measurement with stored gas emission data associated with a category of the group of items; and make a determination corresponding to the group of items based on the comparison.

In some embodiments, a method of automatically monitoring merchandise in a retail sales environment is provided. The method includes a control circuit receiving a gas emission measurement measured with one or more gas emission sensors associated with a display fixture configured to store and display for sale a group of perishable items, comparing the gas emission measurement with stored gas emission data associated with a category of the group of items, making a determination corresponding to the group of items based on the comparing.

Those skilled in the art will recognize that a wide variety of other modifications, alterations, and combinations can also be made with respect to the above described embodiments without departing from the scope of the invention, and that such modifications, alterations, and combinations are to be viewed as being within the ambit of the inventive concept.

What is claimed is:

1. A system for automatically monitoring gas emissions of perishable goods in a retail sales environment comprising:
   a display fixture configured to store and display for sale a group of perishable items;
   one or more gas emission sensors associated with the display fixture and configured to measure gas emissions from the group of perishable items;
   a control circuit coupled to the one or more gas emission sensors and configured to:
      receive a gas emission measurement;
      compare the gas emission measurement with stored gas emission data associated with a category of the group of perishable items; and
      make a determination corresponding to the group of perishable items based on the comparison; and
      determine whether to apply a discount to the group of perishable items based on the determination.

2. The system of claim 1, wherein the group of perishable items comprises one or more of produce, dairy, meat, seafood, plant, floral, deli, prepared meals and bakery goods.

3. The system of claim 1, wherein the category of the group of perishable items corresponds to one or more of a genus, a species, a variety, a cultivar, a growth location, and a growth time.

4. The system of claim 1, wherein the control circuit is further configured to:
   identify the group of perishable items based on the gas emission measurement and determine the category for the group of perishable items.

5. The system of claim 1, wherein the one or more gas emission sensors are integrated into a structure of the display fixture.

6. The system of claim 1, wherein the determination comprises a determination of one or more of: freshness, estimated expiration date, item presence, item location, and item type.

7. The system of claim 1, wherein the stored gas emission data comprises a gas emission over time profile uniquely associated with the category.

8. The system of claim 7, wherein a history of the gas emission measurement is recorded and compared with the stored gas emission data.

9. The system f claim 1, wherein the control circuit is further configured to:
   determine whether to apply a discount to the group of perishable items further based on one or more of a forecasted rate of sales, an expected time between purchase and use by a customer, and incoming inventory information.

10. The system of claim 1, wherein the control circuit is further configured to:
    collect gas emission measurements from a plurality of groups of perishable items and compare the collected gas emission measurements with a planogram of a retail space to determine whether the planogram is followed.

11. A method for automatically monitoring gas emissions of perishable goods in a retail sales environment comprising:
    taking a gas emission measurement with one or more gas emission sensors associated with the display fixture, the display fixture configured to store and display for sale a group of perishable items;

providing the gas emission measurement to a control circuit;

comparing, by the control circuit, the gas emission measurement with stored gas emission data associated with a category of the group of perishable items;

making, by the control circuit, a determination corresponding to the group of perishable items based on the comparing; and determine whether to apply a discount to the group of perishable items based on the determination.

12. The method of claim 11, wherein the group of perishable items comprises one or more of produce, dairy, meat, seafood, plant, floral, deli, prepared meals and bakery goods.

13. The method of claim 11, wherein the category of the group of perishable items corresponds to one or more of a genus, a species, a variety, a cultivar, a growth location, and a growth time.

14. The method of claim 11, further comprising:
identifying the group of perishable items based on the gas emission measurement and determining the category for the group of perishable items.

15. The method of claim 11; wherein the one or more gas emission sensors are integrated into a structure of the display fixture.

16. The method of claim 11, wherein the making the determination step comprises making a determination of one or more of: freshness, estimated expiration date, item presence, item location, and item type.

17. The method of claim 11, wherein the stored gas emission data comprises a gas emission over time profile uniquely associated with the category.

18. The method of claim 17, wherein a history of the gas emission measurement is recorded and compared with the stored gas emission data.

19. The method of claim 11,
wherein whether to apply a discount to the group of perishable items is determined further based on one or more of a forecasted rate of sales, an expected time between purchase and use by a customer, and incoming inventory information.

20. The method of claim 11, further comprising:
collecting gas emission measurements from a plurality of groups of perishable items and comparing the collected gas emission measurements with a planogram of a retail space to determine whether the planogram is followed.

21. An apparatus for automatically monitoring gas emissions of perishable goods in a retail sales environment comprising:
a control circuit; and
a non-transitory computer readable memory storing a set of instructions executable by the control circuit and configured to cause the control circuit to perform the steps of:
receive a gas emission measurement measured with one or more gas emission sensors associated with a display fixture configured to store and display for sale a group of perishable items;
compare the gas emission measurement with stored gas emission data associated with a category of the group of perishable items;
make a determination corresponding to the group of perishable items based on the comparison; and
determine whether to apply a discount to the group of perishable items based on the determination.

22. A method of automatically monitoring gas emissions of perishable goods in a retail sales environment comprising:
by a control circuit,
receiving a gas emission measurement measured with one or more gas emission sensors associated with a display fixture configured to store and display for sale a group of perishable items;
comparing the gas emission measurement with stored gas emission data associated with a category of the group of perishable items;
making a determination corresponding to the group of perishable items based on the comparing; and
determining whether to apply a discount to the group of perishable items based on the determination.

* * * * *

UNITED STATES PATENT AND TRADEMARK OFFICE
CERTIFICATE OF CORRECTION

PATENT NO. : 11,070,895 B2  
APPLICATION NO. : 15/990397  
DATED : July 20, 2021  
INVENTOR(S) : Joseph D. Taylor Page 1 of 1

It is certified that error appears in the above-identified patent and that said Letters Patent is hereby corrected as shown below:

In the Claims

In Claim 9, delete "system f claim 1" and insert -- system of claim 1 --, therefor.

In Claim 15, delete "claim 11;" and insert -- claim 11, --, therefor.

Signed and Sealed this  
Eleventh Day of January, 2022

Drew Hirshfeld  
*Performing the Functions and Duties of the*  
*Under Secretary of Commerce for Intellectual Property and*  
*Director of the United States Patent and Trademark Office*